(12) United States Patent
Sweeney et al.

(10) Patent No.: US 7,792,571 B2
(45) Date of Patent: Sep. 7, 2010

(54) TACHYARRHYTHMIA DETECTION AND DISCRIMINATION BASED ON CURVATURE PARAMETERS

(75) Inventors: Robert J. Sweeney, Woodbury, MN (US); Carlos Ricci, Apple Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1567 days.

(21) Appl. No.: 10/607,818

(22) Filed: Jun. 27, 2003

(65) Prior Publication Data

US 2007/0203419 A1   Aug. 30, 2007

(51) Int. Cl.
*A61B 5/04*      (2006.01)
(52) U.S. Cl. .................. 600/509; 600/515; 600/516; 600/517
(58) Field of Classification Search .......... 600/515, 600/516, 518, 510, 509; 607/4, 5, 14
See application file for complete search history.

(56) References Cited

U.S. PATENT DOCUMENTS

| | | | |
|---|---|---|---|
| 4,336,810 A | | 6/1982 | Anderson et al. |
| 4,523,595 A | * | 6/1985 | Zibell ............................. 607/5 |
| 4,583,553 A | | 4/1986 | Shah et al. |
| 4,637,400 A | | 1/1987 | Marcus |
| 4,721,114 A | | 1/1988 | DuFault et al. |
| 4,802,491 A | | 2/1989 | Cohen et al. |
| 4,825,869 A | | 5/1989 | Sasmor et al. |
| 4,832,038 A | | 5/1989 | Arai et al. |
| 4,838,278 A | | 6/1989 | Wang et al. |
| 4,924,875 A | | 5/1990 | Chamoun |
| 4,947,857 A | | 8/1990 | Albert et al. |
| 4,996,984 A | * | 3/1991 | Sweeney ........................ 607/5 |

(Continued)

FOREIGN PATENT DOCUMENTS

DE    4405827    6/1995

(Continued)

OTHER PUBLICATIONS

"U.S. Appl. No. 10/607,820 Amendment and Response filed Apr. 19, 2007 to Non-Final Office Action mailed Nov. 22, 2006", 15 pgs.

(Continued)

*Primary Examiner*—Carl H Layno
*Assistant Examiner*—Joseph Stoklosa
(74) *Attorney, Agent, or Firm*—Schwegman, Lundberg & Woessner, P.A.

(57) ABSTRACT

Estimating a frequency of a sampled cardiac rhythm signal and classifying the rhythm. The received signal is sampled and transformed into a curvature series. A lobe in the curvature series corresponds to a characteristic point in the sampled series. Characteristic points are selected based on a time of a lobe in the curvature series and, in one embodiment, an amplitude of the signal at the time of the lobe. A frequency of the sampled series is estimated by autocorrelating a function of the series of the characteristic points. In one embodiment, the function is a time difference function. The rhythm is classified by plotting the timewise proximity of characteristic points derived from an atrial signal with characteristic points derived from a ventricular signal. Regions of the plot are associated with a particular rhythm and the grouping of the data corresponds to the classification.

25 Claims, 13 Drawing Sheets

U.S. PATENT DOCUMENTS

| | | | |
|---|---|---|---|
| 5,014,284 A | 5/1991 | Langer et al. | |
| 5,046,504 A | 9/1991 | Albert et al. | |
| 5,184,615 A | 2/1993 | Nappholz et al. | |
| 5,193,550 A | 3/1993 | Duffin | |
| 5,201,321 A | 4/1993 | Fulton | |
| 5,217,021 A | 6/1993 | Steinhaus et al. | |
| 5,228,438 A | 7/1993 | Buchanan | |
| 5,240,009 A | 8/1993 | Williams | |
| 5,271,411 A | 12/1993 | Ripley et al. | |
| 5,273,049 A | 12/1993 | Steinhaus et al. | |
| 5,275,621 A | 1/1994 | Mehra | |
| 5,280,792 A | 1/1994 | Leong et al. | |
| 5,291,400 A | 3/1994 | Gilham | |
| 5,292,341 A | 3/1994 | Snell | |
| 5,292,348 A | 3/1994 | Saumarez et al. | |
| 5,311,874 A | 5/1994 | Baumann et al. | |
| 5,312,445 A | 5/1994 | Nappholz et al. | |
| 5,313,953 A | 5/1994 | Yomtov et al. | |
| 5,330,504 A | 7/1994 | Somerville et al. | |
| 5,331,966 A | 7/1994 | Bennett et al. | |
| 5,334,220 A | 8/1994 | Sholder | |
| 5,342,402 A | 8/1994 | Olson et al. | |
| 5,350,406 A | 9/1994 | Nitzsche et al. | |
| 5,351,696 A | 10/1994 | Riff et al. | |
| 5,360,436 A | 11/1994 | Alt et al. | |
| 5,365,934 A * | 11/1994 | Leon et al. | 600/517 |
| 5,366,487 A | 11/1994 | Adams et al. | |
| 5,383,910 A | 1/1995 | den Dulk | |
| 5,387,229 A | 2/1995 | Poore | |
| 5,391,189 A | 2/1995 | van Krieken et al. | |
| 5,400,795 A | 3/1995 | Murphy et al. | |
| 5,411,031 A | 5/1995 | Yomtov | |
| 5,417,714 A | 5/1995 | Levine et al. | |
| 5,431,693 A | 7/1995 | Schroeppel | |
| 5,447,519 A | 9/1995 | Peterson | |
| 5,458,620 A | 10/1995 | Adams et al. | |
| 5,464,433 A | 11/1995 | White et al. | |
| 5,480,412 A | 1/1996 | Mouchawar et al. | |
| 5,487,754 A | 1/1996 | Snell et al. | |
| 5,503,159 A | 4/1996 | Burton | |
| 5,511,554 A | 4/1996 | Helfenbein et al. | |
| 5,513,644 A | 5/1996 | McClure et al. | |
| 5,514,163 A | 5/1996 | Markowitz et al. | |
| 5,520,191 A | 5/1996 | Karlsson et al. | |
| 5,542,430 A | 8/1996 | Farrugia et al. | |
| 5,545,186 A | 8/1996 | Olson et al. | |
| 5,549,641 A | 8/1996 | Ayers et al. | |
| 5,560,369 A | 10/1996 | McClure et al. | |
| 5,603,331 A | 2/1997 | Heemels et al. | |
| 5,605,159 A | 2/1997 | Smith et al. | |
| 5,628,326 A | 5/1997 | Arand et al. | |
| 5,645,070 A | 7/1997 | Turcott | |
| 5,676,153 A | 10/1997 | Smith et al. | |
| 5,682,900 A | 11/1997 | Arand et al. | |
| 5,685,315 A | 11/1997 | McClure et al. | |
| 5,697,959 A | 12/1997 | Poore | |
| 5,704,365 A | 1/1998 | Albrecht et al. | |
| 5,712,801 A | 1/1998 | Turcott | |
| 5,713,367 A | 2/1998 | Arnold et al. | |
| 5,718,242 A | 2/1998 | McClure et al. | |
| 5,730,142 A | 3/1998 | Sun et al. | |
| 5,738,105 A | 4/1998 | Kroll | |
| 5,749,900 A | 5/1998 | Schroeppel et al. | |
| 5,755,739 A | 5/1998 | Sun et al. | |
| 5,778,881 A | 7/1998 | Sun et al. | |
| 5,779,645 A | 7/1998 | Olson et al. | |
| 5,782,888 A | 7/1998 | Sun et al. | |
| 5,788,717 A | 8/1998 | Mann et al. | |
| 5,792,065 A | 8/1998 | Xue et al. | |
| 5,792,066 A | 8/1998 | Kwong | |
| 5,795,303 A | 8/1998 | Swanson et al. | |
| 5,797,399 A | 8/1998 | Morris et al. | |
| 5,810,739 A | 9/1998 | Bornzin et al. | |
| 5,814,077 A | 9/1998 | Sholder et al. | |
| 5,817,133 A | 10/1998 | Houben | |
| 5,819,007 A | 10/1998 | Elghazzawi | |
| 5,819,741 A | 10/1998 | Karlsson et al. | |
| 5,827,195 A | 10/1998 | Lander | |
| 5,836,889 A | 11/1998 | Wyborny et al. | |
| 5,836,987 A | 11/1998 | Baumann et al. | |
| 5,855,593 A | 1/1999 | Olson et al. | |
| 5,857,977 A | 1/1999 | Caswell et al. | |
| 5,868,680 A | 2/1999 | Steiner et al. | |
| 5,873,897 A | 2/1999 | Armstrong et al. | |
| 5,873,898 A | 2/1999 | Hemming et al. | |
| 5,935,082 A | 8/1999 | Albrecht et al. | |
| 5,941,831 A | 8/1999 | Turcott | |
| 5,944,744 A | 8/1999 | Paul et al. | |
| 5,951,592 A | 9/1999 | Murphy | |
| 5,954,661 A | 9/1999 | Greenspon et al. | |
| 5,978,700 A | 11/1999 | Nigam | |
| 5,978,707 A | 11/1999 | Krig et al. | |
| 5,983,138 A | 11/1999 | Kramer | |
| 5,991,656 A | 11/1999 | Olson et al. | |
| 5,991,657 A | 11/1999 | Kim | |
| 6,016,442 A | 1/2000 | Hsu et al. | |
| 6,024,705 A | 2/2000 | Schlager et al. | |
| 6,049,735 A | 4/2000 | Hartley et al. | |
| 6,052,617 A | 4/2000 | Kim | |
| 6,076,014 A | 6/2000 | Alt | |
| 6,081,745 A | 6/2000 | Mehra | |
| 6,091,990 A | 7/2000 | Hsu et al. | |
| 6,192,273 B1 | 2/2001 | Igel et al. | |
| 6,212,428 B1 | 4/2001 | Hsu et al. | |
| 6,223,078 B1 | 4/2001 | Marcovecchio | |
| 6,233,487 B1 | 5/2001 | Mika et al. | |
| 6,253,102 B1 | 6/2001 | Hsu et al. | |
| 6,263,242 B1 | 7/2001 | Mika et al. | |
| 6,266,554 B1 | 7/2001 | Hsu et al. | |
| 6,272,377 B1 | 8/2001 | Sweeney et al. | |
| 6,275,732 B1 | 8/2001 | Hsu et al. | |
| 6,301,499 B1 | 10/2001 | Carlson et al. | |
| 6,301,503 B1 | 10/2001 | Hsu et al. | |
| 6,308,095 B1 | 10/2001 | Hsu et al. | |
| 6,312,388 B1 | 11/2001 | Marcovecchio et al. | |
| 6,370,430 B1 | 4/2002 | Mika et al. | |
| 6,400,982 B2 | 6/2002 | Sweeney et al. | |
| 6,430,435 B1 | 8/2002 | Hsu et al. | |
| 6,430,438 B1 | 8/2002 | Chen et al. | |
| 6,434,417 B1 | 8/2002 | Lovett | |
| 6,438,410 B2 | 8/2002 | Hsu et al. | |
| 6,449,503 B1 | 9/2002 | Hsu | |
| 6,470,210 B1 | 10/2002 | Chen et al. | |
| 6,484,055 B1 | 11/2002 | Marcovecchio | |
| 6,516,219 B1 | 2/2003 | Street | |
| 6,516,225 B1 | 2/2003 | Florio | |
| 6,539,257 B1 | 3/2003 | KenKnight | |
| 6,571,121 B2 | 5/2003 | Schroeppel et al. | |
| 6,684,100 B1 | 1/2004 | Sweeney et al. | |
| 6,950,702 B2 | 9/2005 | Sweeney | |
| 7,500,955 B2 | 3/2009 | Sweeney | |
| 2002/0193696 A1 | 12/2002 | Hsu et al. | |
| 2003/0069511 A1* | 4/2003 | Stridh et al. | 600/515 |
| 2004/0010200 A1 | 1/2004 | Sweeny et al. | |
| 2004/0127806 A1 | 7/2004 | Sweeney | |
| 2004/0215244 A1* | 10/2004 | Marcovecchio et al. | 607/5 |
| 2004/0267143 A1 | 12/2004 | Sweeny | |
| 2005/0159781 A1 | 7/2005 | Hsu | |

FOREIGN PATENT DOCUMENTS

| | | |
|---|---|---|
| EP | 469817 A2 | 7/1991 |
| EP | 506230 A1 | 2/1992 |
| EP | 554208 | 8/1993 |

| WO | WO-97/39681 A1 | 10/1997 |
| WO | WO-99/65570 | 12/1999 |
| WO | WO-99/65570 A1 | 12/1999 |
| WO | WO-00/10455 | 3/2000 |
| WO | WO-00/10455 A1 | 3/2000 |
| WO | WO-00/47278 | 8/2000 |
| WO | WO-00/47278 A1 | 8/2000 |
| WO | WO-0141870 A2 | 6/2001 |
| WO | WO-02/40094 A2 | 5/2002 |
| WO | WO-0240094 A2 | 5/2002 |
| WO | WO-2005/002669 A2 | 1/2005 |

OTHER PUBLICATIONS

"Non-Final Office Action mailed Nov. 12, 2004 in U.S. Appl. No. 10/195,838", 6 pgs.

"Non-Final Office Action mailed Nov. 22, 2006 in U.S. Appl. No. 10/607,820", 16 pgs.

"Non-Final Office Action mailed Nov. 29, 2002 in U.S. Appl. No. 09/703,269", 6 pgs.

"Non-Final Office Action mailed Jun. 20, 2002 in U.S. Appl. No. 09/703,269", 4 pgs.

"Non-Final Office Action mailed Jul. 1, 2003 in U.S. Appl. No. 09/703,269", 6 pgs.

"Notice of Allowance mailed Sep. 8, 2003 in U.S. Appl. No. 09/703,269", 10 pgs.

"U.S. Appl. No. 09/703,269 Response filed Sep. 20, 2002 to Non-Final Office Action mailed Jun. 20, 2002", 3 pgs.

"U.S. Appl. No. 09/703,269 Response filed Mar. 31, 2003 to Non-Final Office Action mailed Nov. 29, 2002", 12 pgs.

"International Search Report for PCT Application No. PCT/US2004/020723", (Feb. 8, 2005),7 pgs.

"Written Opinion for PCT Application No. PCT/US2004/020723",12 pgs.

Vapnik, V. N., "Chapter 5 Constructing Learning Algorithms", *The Nature of Statistical Learning Theory*, Springer-Verlag New York, Inc.,(1995),119-166.

"European Application Serial No. 1984963.7, Communication mailed Oct. 6, 2008", 4 pgs.

2004-521816, "Japanese Application Serial No. 200-521816, Office Action mailed Mar. 30, 2009", 7.

\* cited by examiner

TACHYARRHYTHMIA DETECTION AND DISCRIMINATION BASED ON CURVATURE PARAMETERS

RELATED APPLICATIONS

This document is related to and commonly assigned U.S. patent application Ser. No. 09/703,269, entitled "CURVATURE BASED METHOD FOR SELECTING FEATURES FROM AN ELECTROPHYSIOLOGICAL SIGNALS FOR PURPOSE OF COMPLEX IDENTIFICATION AND CLASSIFICATION," inventor Sweeney et al., filed on Oct. 31, 2000, now issued as U.S. Pat. No. 6,684,100, the specification of which is hereby incorporated by reference in its entirety.

This document is related to and commonly assigned U.S. patent application Ser. No. 10/195,838, entitled "USE OF CURVATURE BASED FEATURES FOR BEAT DETECTION," inventor Sweeney, filed on Jul. 15, 2002, now issued as U.S. Pat. No. 6,950,702, the specification of which is hereby incorporated by reference in its entirety.

This document is related to co-pending and commonly assigned U.S. patent application Ser. No. 10/607,820 entitled "SIGNAL COMPRESSION BASED ON CURVATURE PARAMETERS," inventor Sweeney, filed on Jun. 27, 2003, the specification of which is hereby incorporated by reference in its entirety.

TECHNICAL FIELD

This document relates generally to cardiac rhythm management and in particular, but not by way of limitation, to detection and discrimination of arrhythmias in an implantable medical device.

BACKGROUND

Implantable cardiac rhythm management devices typically monitor and process cardiac signals to provide therapy to the heart. Therapy may include delivering a pacing pulse to trigger a contraction of the heart or delivering a defibrillation shock to interrupt an abnormal heart rhythm. Some cardiac rhythm management devices also monitor cardiac performance or other physiological parameters for use in controlling the delivery of pacing pulses.

Before delivering therapy, some implantable cardiac rhythm management devices are programmed to verify that an arrhythmia is occurring. In addition, therapy can be tailored to the patient's needs if the rhythm type is known.

There exists an unmet need for providing improved arrhythmia detection and discrimination systems, devices, and methods to allow better diagnosis or treatment of patients.

SUMMARY

The present subject matter provides a curvature based method of selecting features from a sampled signal. In one embodiment, the sampled signal includes a cardiac signal or an electrocardiogram. According to one aspect of the present subject matter, characteristic points are selected by sensing a cardiac signal on a real-time basis and upon receipt of each sample, computing curvatures on a continuous basis. Characteristic points are sometimes referred to as significant points or data points.

In one embodiment, each "turn" in the signal is represented with a characteristic point that has measures of time, value, area and width. Time refers to a time denoting the center of the turn in the curvature series. Value refers to the amplitude of the input signal at the time of the center of the turn. Area refers to a value denoting the direction and degree of the turn. Width refers to a value denoting the duration over which the turn occurs.

By the methods presented herein, each new characteristic point is known as soon as the turn which it describes has ended. In one embodiment, the stream of characteristic points are analyzed continuously as each new characteristic point occurs. In one embodiment, the characteristic points are saved into a buffer for analysis at a later time.

All turns in an input signal are not the same. Some turns may be large deflections with sharp angles (for example, turns in a QRS signal) while other turns might be slight and not associated with big deflections (for example, noise in the signal). In one embodiment, the present subject matter includes a scheme to select prominent characteristic points in a signal and discard the smaller ones that may represent noise or only slight signal deflections.

The area for the characteristic point is an indirect measure of the angular turn in the signal. The maximum turn is approximately 180 degrees which represents a very rapid signal reversal. A large deflection in the signal, such as the R-wave (a full signal swing in 10 samples over, a period of 50 ms) would have large turn angle of 178 degrees. A small noise spike (such as a 10% full scale swing for a single sample) may also have a large turn angle of 175 degrees. The present subject matter treats these signal deflections differently. The R-wave has a large area whereas the noise spike would have a small area since it occurred over a lower number of samples. Thus, the characteristic point area is a surrogate for determining which characteristic points are important and which are not.

The effect of the foregoing is that small characteristic points at or near the signal baseline value are ignored. According to one embodiment, an absolute area threshold value in the range of 0.5 is used for a rate-sensing channel.

In one embodiment, the present subject matter automatically adjusts the threshold value to better adapt to varying patients and signals.

In one embodiment, each characteristic point includes a time component, an amplitude component and an area component. According to the present subject matter, the time, amplitude and area components are derived from a curvature calculation performed using the sampled signal.

Typical cardiac rhythm management devices determine the heart rate by sensing beats in a cardiac electrical signal and detecting when an R wave occurs in the signal. An R wave (sometimes referred to as a QRS complex) represents the major electrical event for each beat of the heart. In one embodiment, the plurality of characteristic points are analyzed to determine a heart rate without relying on beat sensing. In one embodiment, a first estimate of heart rate is generated by autocorrelating a particular function of characteristic points. In one embodiment, a time difference autocorrelation function yields the heart rate. In one embodiment, a second estimate of the heart rate (or beat frequency) is generated by a secondary process and the two estimates are reconciled to derive a single value for the heart rate.

In one embodiment, an atrial series of characteristic points are generated for an atrial channel and a ventricular series of characteristic points are generated for a ventricular channel. The relative timing of the atrial series and the ventricular series are compared and the comparison forms the basis for discriminating among different rhythm types. Other methods are also contemplated including discriminating on the basis of variations in characteristic point timing and cross-correlations in the characteristic point domain.

In one embodiment, a window is established before each ventricular characteristic point. Relative timing is evaluated by counting atrial and ventricular characteristic points relative to the windows and graphically plotting the results on a grid. The grid is divided into regions corresponding to different rhythm types.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present subject matter. The following detailed description is, therefore, not to be taken in a limiting sense, and the scope of the present invention is defined by the appended claims and their equivalents.

This document discloses, among other things, systems, method and apparatus involving cardiac rhythm management systems used for sensing a cardiac signal, including intracardiac electrogram or surface electrocardiogram (ECG). Such cardiac rhythm management systems include, but are not limited to, pacemakers, CRT devices, cardioverter/defibrillators, pacer/defibrillators, and drug delivery devices. However, it is to be understood that the present methods and apparatuses of compressing a signal can be applied to heart beat detection as well as other signals related to cardiac activities, including, but not being limited to, mechanical motion, sound, pressure, acceleration, and impedance signals.

Curvature Based Analysis

Figure 1:
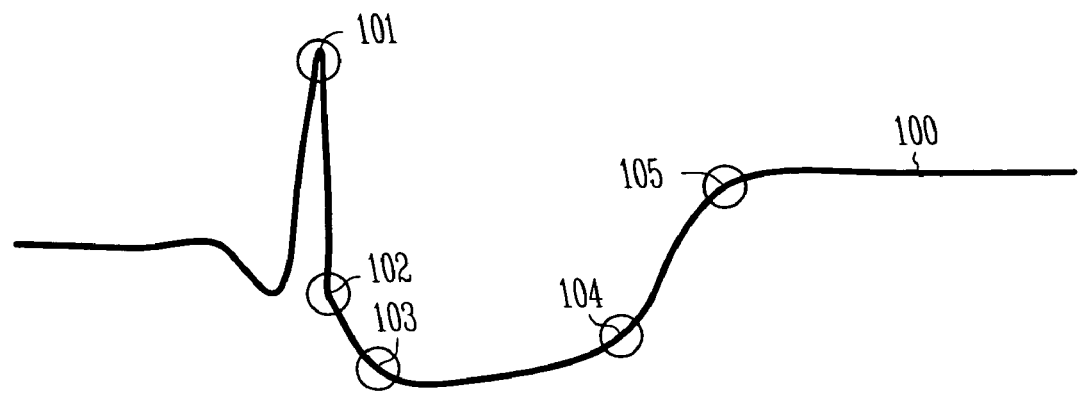
FIG. 1 illustrates an arbitrary signal as a function of time.

For an arbitrary voltage versus time signal, the salient characteristics can be captured in terms of those points along the signal where it makes characteristic "turns." In general, these points are different from those that would be selected using first or second derivative criteria as shown in FIG. 1. In the figure, which illustrates arbitrary electrogram 100, the R wave, denoted as point 101, has a high second derivative $d^2V/dt^2$. Further, the electrogram sections on either side of point 101 have high positive and negative slopes detectable with a first derivative criteria. However, those points with these large (or even maximum) slopes do not convey any particularly significant description of the electrogram. For example, at each time along a segment between points 101 and 102, the waveform has a large negative slope but no point along this segment stands out significantly from any other.

On the other hand, points 102, 103, 104 and 105 are neither maximums nor minimums of the electrogram or its derivatives. These points are descriptive of the arbitrary waveform shape. Points 102, 103, 104 and 105 are salient because they mark locations where the signal makes significant turns. The turn at point 101 is very sharp and the turns at points 103 and 105 are less sharp turns and more broad. The turns at points 102 and 104 are even less sharp but rather local. The present subject matter detects points 101, 102, 103, 104 and 105 using a criteria based on the curvature of the signal.

Figure 2:
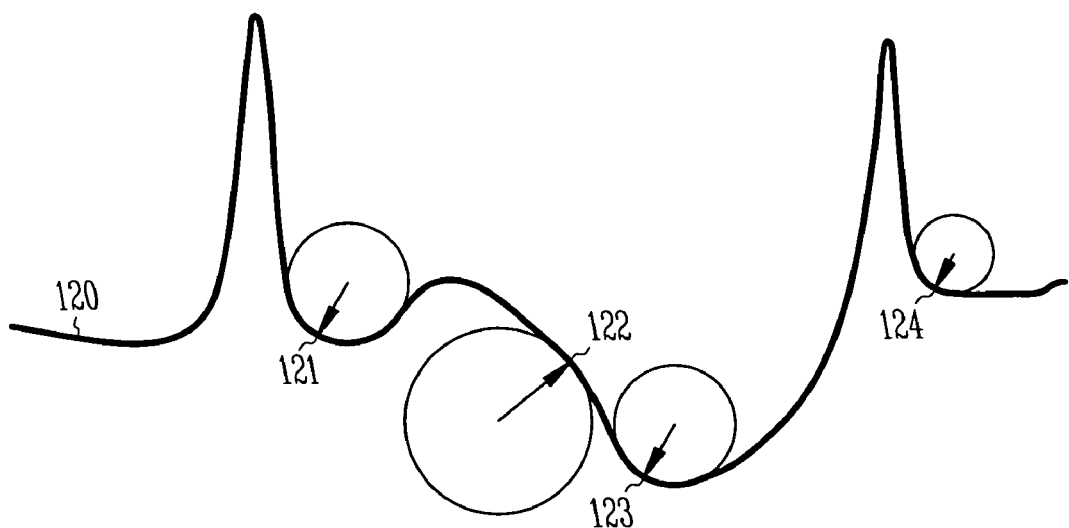
FIG. 2 illustrates osculating circles fitted to an arbitrary signal as a function of time.

According to one embodiment of the present subject matter, signal curvature is illustrated in FIG. 2. In the figure, arbitrary electrogram 120 is shown. At each point along electrogram 120, an osculating circle can be found that fits tangentially with the local portion of the electrogram. Each circle has a radius. The curvature of electrogram 120 at that point is the inverse of that radius so that small circles have large curvatures while large circles have small curvature. FIG. 2 shows these circles at selected points. At point 122, the circle is larger, and thus the curvature is smaller, than at points 121, 123 and 124. At points 121, 123 and 124, the turns are sharper and the curvature is larger.

In general, the curvature at point (X, Y) of an arbitrary curve in a two-dimensional space is expressed as:

$$\text{Curvature} = \frac{\frac{d^2Y}{dX^2}}{\left[1 + \left\{\frac{dY}{dX}\right\}^2\right]^{3/2}}.$$

As seen, the curvature is a non-linear combination of both the first and second derivatives of the curve. At those points along the curve where the first derivative is zero (for example, point 101 in FIG. 1), the curvature is equal to the second derivative and at points where the second derivative is zero (for example, any straight section regardless of its slope), the curvature is zero.

The present subject matter calculates curvature of an arbitrary input signal on a sample-by-sample basis.

Consider the question of dimensionality of the curvature for electrogram signals. When both X and Y have the same dimensions (say length) then curvature has a dimension of 1/length. For an arbitrary signal having a voltage as a function of time V(t), such as an electrocardiogram, the signal is transformed into a time-versus-time signal T(t) according to T(t)=V(t)/U where U is a constant with dimensions of voltage/time. With this transformation, the first and second derivatives of T(t) become $$\frac{dT(t)}{dt} = \frac{dV(t)}{dt} \cdot 1/U$$

which is dimensionless and $$\frac{d^2 T(t)}{dt^2} = \frac{d^2 V(t)}{dt^2} \cdot 1/U$$

which has dimensions of 1/time and thus the curvature has dimensions of 1/time. Curvature is then expressed as:

$$\text{Curvature} = \frac{\frac{d^2 T(t)}{dt^2}}{\left[1 + \left\{\frac{dT(t)}{dt}\right\}^2\right]^{3/2}} = \frac{d^2 V(t)/dt^2 / U}{[1 + \{dV(t)/dt/U\}^2]^{3/2}}$$

which has dimensions of 1/time and U has a numerical value.

Consider next, curvature as a function of signal gain or amplitude of the input signal. Assume arbitrary gain G is applied to the input signal to find a new input signal F(t) wherein F(t)=G·T(t)=V(t)·G/U. The curvature of the gained signal is then:

$$\text{Curvature} = \frac{\frac{d^2 F(t)}{dt^2}}{\left[1 + \left\{\frac{dF(t)}{dt}\right\}^2\right]^{3/2}} = \frac{d^2 V(t)/dt^2 \cdot G/U}{[1 + \{dV(t)/dt \cdot G/U\}^2]^{3/2}}.$$

The ratio G/U can be expressed as W having dimensions of time/voltage. In one embodiment, the input signal is a voltage sampled with a 12-bit analog-to-digital converter (ADC) having numerical voltage values in the range +/−2048 where each value represents a number of basic amplitude units $\Delta V$, or voltage resolution. In one embodiment, the amplifiers in the present subject matter are adjusted so that the samples from V(t) largely fill this range. Furthermore, it is assumed that the samples are taken at a fixed rate and thus the time is represented by an integer number of samples with each sample representing a time interval $\Delta T$=time resolution=1/(sample rate).

Figure 3:
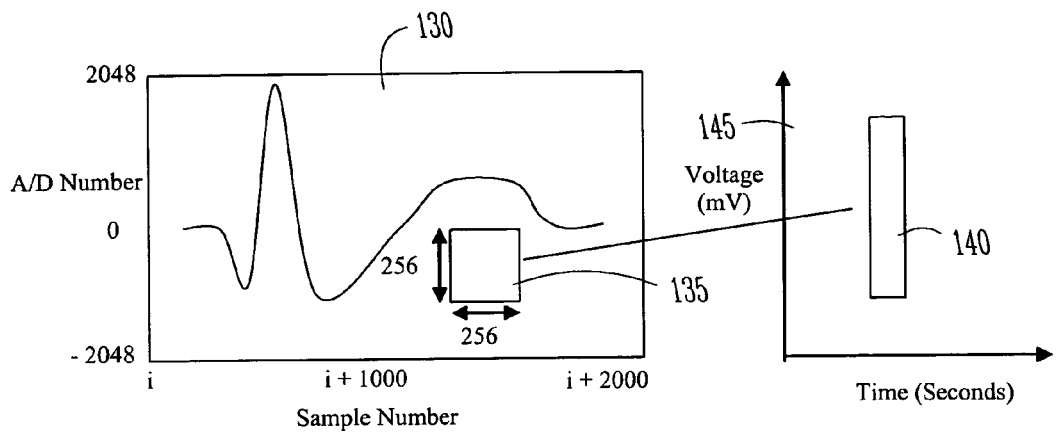
FIG. 3 illustrates a signal expressed in analog-to-digital converter value as a function of sample number.

FIG. 3 illustrates numerical X-Y space 130 which is denoted by sample numbers on the X-axis and the analog-to-digital conversion value on the Y-axis. Consider square 135 in X-Y space 130 which is 256 steps along the X-axis and 256 steps along the Y-axis and rectangle 140 in voltage-time space 145 that this square represents. Rectangle 140 has a width of 256/(sample rate), in seconds and a height of 256/(voltage resolution), in volts. Depending on the values selected for $\Delta V$ and $\Delta T$, this rectangle may or may not be a square in voltage-time space.

In one embodiment, W is selected to require that a square in voltage-time space be represented by a square in sample-sample space. Under that condition, the curvature versus time relationships that exist in voltage-time space are preserved in sample-sample space.

Figure 4:
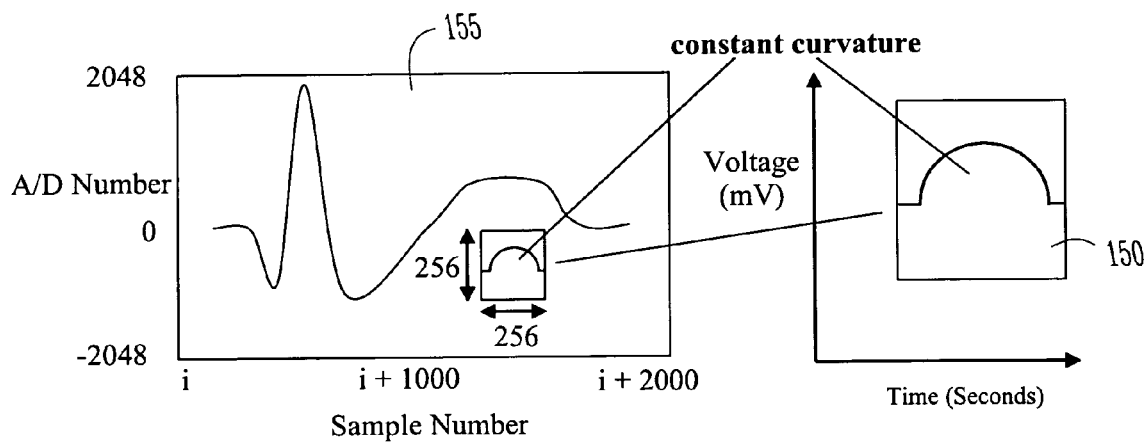
FIG. 4 illustrates a signal expressed in analog-to-digital converter value as a function of sample number and having a constant curvature.

In FIG. 4, an artificial voltage-time curve is shown that forms a semicircle inside square box 150. Traversing from left to right across box 150 in voltage time space, the curvature of the signal is zero until the semicircle is encountered. The curvature jumps to a constant value, equal to 1/radius of the circle, and again jumps to zero at the end of the semicircle. For a particular value of W, the representation of this signal in sample-sample space 155 also has a constant curvature and for other values of W, the curvature would not be constant in sample-sample space.

To maintain this relationship between voltage-time and sample-sample space, W is selected as follows. In voltage-time space, the box T wide by V high is taken to be square. In sample-sample space, the box is T/$\Delta T$ time-samples wide and GV/$\Delta V$ voltage-samples high and through a transformation, the voltage sample is converted into time-samples using U so that the sample-space square has dimensions of T/$\Delta T$ by VG/$\Delta V$/U. For the box to be square in sample-space, and assuming the box (V by T) in voltage-time space is square, then (V/$\Delta V$). G/U=T/$\Delta T$ or G/U=W=(T/$\Delta T$)/(V/$\Delta V$).

According to one embodiment of the present subject matter, curvature is based on the first and second derivative of the signal. A least square cubic polynomial fit is used to reduce the noise that would otherwise result from using numerical estimates for the derivatives and using non-linear calculations to find curvature.

The sampled voltage signal is expressed as V(t)=V(I·$\Delta T$) where t=i·$\Delta T$ so that the fit of size N uses 2N+1 voltage samples centered on the time t, thus:

V([i−n]·$\Delta T$), ... V([i−2]·$\Delta T$),V([i−1]·$\Delta T$),V(i·$\Delta T$),
    V([i+1]·$\Delta T$),V([i+2]·$\Delta T$), ... V([i+n]·$\Delta T$).

This set of N sampled data points is used to make the least-squares cubic fit which is given as $V_{est}$ [i·$\Delta T$+dt]=Ai+Bi·[dt]+Ci·[dt]$^2$+Di·[dt]$^3$ where Ai, Bi, Ci, and Di are coefficients determined by minimizing the square error for the fit and dt represents a time step away from i·$\Delta T$ at which $V_{est}$ is evaluated. The coefficients in the polynomial are denoted with an i to indicate that they are valid for the point i $\Delta T$.

Using the above equations, the curvature on a point to point basis, at the time i·$\Delta T$, becomes $$\text{Curvature}(i \cdot \Delta T) = \frac{\frac{d^2 V(t)}{dt^2} \cdot W}{\left[1 + \left\{\frac{dV(t)}{dt} \cdot W\right\}^2\right]^{3/2}} = \frac{2 \cdot Ci \cdot W}{[1 + \{Bi \cdot W\}^2]^{3/2}}.$$

Sample points, however, will not necessarily fall at the times where the signal curvature has a maximum or minimum value. Thus, in one embodiment, the curvature signal is integrated between adjacent sample points using estimates for the first and second derivative of the signal at the sample points.

Further simplification yields an expression for average point curvature as:

$$Cavg_i = \frac{1}{(B_i - B_{i-1})^2} \cdot \left\{ \frac{C_{i-1} \cdot B_i^2 - C_i \cdot B_i \cdot B_{i-1} - C_i + C_{i-1}}{(B_i^2 + 1)^{1/2}} + \frac{C_i \cdot B_{i-1}^2 - C_{i-1} \cdot B_{i-1} \cdot B_i + C_i - C_{i-1}}{(B_{i-1}^2 + 1)^{1/2}} \right\}, B_i \neq B_{i-1}$$

$$Cavg_i = \frac{1}{2} \cdot \frac{C_i + C_{i-1}}{(B_i^2 + 1)^{3/2}}, B_i = B_{i-1}$$

As noted, curvature is computed on a sample-by-sample basis from the input signal.

Consider next, a procedure for finding the characteristic points in the signal.

Figure 5:
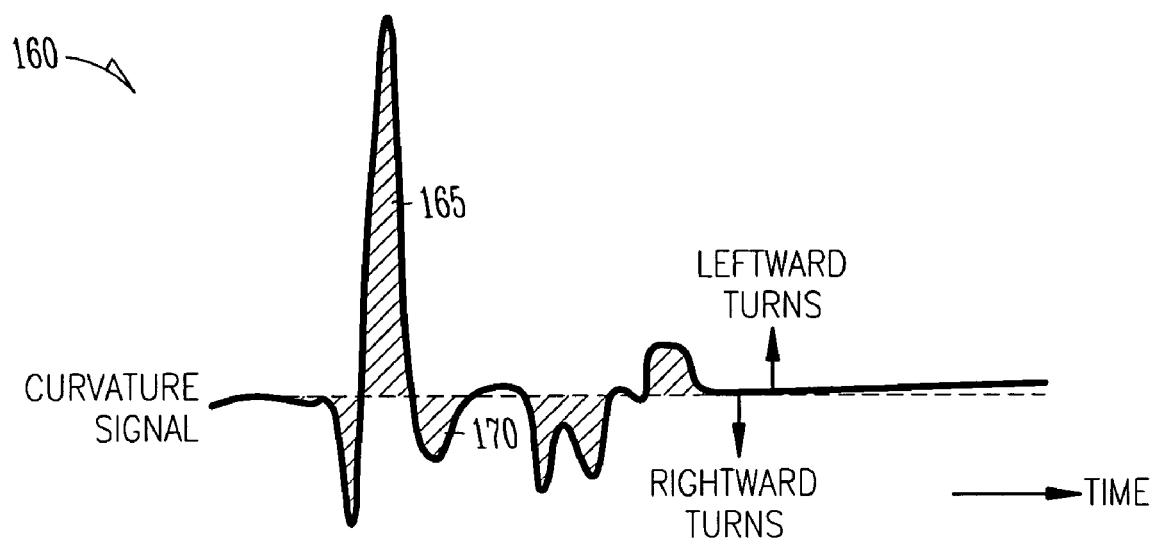
FIG. 5 illustrates lobes of a curvature signal as a function of time.

Turns in the original signal are reflected as excursions above and below zero in the curvature signal. As suggested by curvature 160 of FIG. 5, each lobe above zero (for example, lobe 165) or below zero (for example, lobe 170) then represents a single turn in the input signal. Curvature lobes of opposite directions reflect opposite turns (leftward or rightward) in the signal. The area under each lobe reflects the total angle included in the turn.

A point-by-point method is used to identify the lobes as they occur and to find the area and centroid of each lobe.

Curvature values are generated on a sample by sample basis. At each sample time, CRV represents the current curvature value and $CRV_{old}$ represents the previous value that is retained from the previous sample. When the curvature value is zero, the original signal is not turning so that no characteristic points may exist. The value CRV will rarely be exactly equal to zero.

In one embodiment, a dead-zone surrounding zero is defined where the calculated curvature may be treated as equal to zero. For times where the curvature is within the zone, the signal is not turning significantly. The zone is defined with a curvature threshold value and extends above and below zero from $+CRV_{thresh}$ to $-CRV_{thresh}$.

In one embodiment, the present subject matter identifies nine cases for considering the value of CRV relative to the threshold and the absence or direction of a lobe. These cases can be described as follows:

Case 1: $CRV > CRV_{thresh}$ and not in a Lobe.

Here, the current curvature value is above the dead-zone and the curvature signal is not currently in a lobe. Thus, a positive lobe has just started so the positive lobe initialization calculations will follow.

Case 2: $CRV_{thresh} \geq CRV \geq -CRV_{thresh}$ and not in a Lobe.

Here, the current curvature values is inside the dead-zone and the curvature signal is not currently in a lobe.

Case 3: $CRV < -CRV_{thresh}$ and not in a Lobe.

Here, the current curvature value is below the dead-zone and the curvature signal is not currently in a lobe. Thus, a negative lobe has just started so the negative lobe initialization calculations will follow.

Case 4: $CRV > CRV_{thresh}$ and in a Positive Lobe.

Here, the current curvature value is above the dead-zone and the curvature signal is in a positive lobe. Thus, the positive lobe continuation calculations will follow.

Case 5: $CRV_{thresh} \geq CRV \geq -CRV_{thresh}$ and in a Positive Lobe.

Here, the current curvature value is inside the dead-zone and the curvature signal is in a positive lobe. Thus, a positive lobe has just ended so the positive lobe finalization calculations will follow.

Case 6: $CRV < -CRV_{thresh}$ and in a Positive Lobe.

Here, the current curvature value is below the dead-zone and the curvature signal is currently in a positive lobe. Thus, a positive lobe has just ended and a negative lobe has just started so that both the positive lobe finalization calculations and the negative lobe initialization calculations will follow.

Case 7: $CRV > CRV_{thresh}$ and in a Negative Lobe.

Here, the current curvature value is above the dead-zone and the curvature signal is in a negative lobe. Thus, a negative lobe has just ended and a positive lobe has just started so that both the negative lobe finalization calculations and the positive lobe initialization calculations will follow.

Case 8: $CRV_{thresh} \geq CRV \geq -CRV_{thresh}$ and in a Negative Lobe.

Here, the current curvature value is inside the dead-zone and the curvature signal is in a negative lobe. Thus, a lobe has just ended so the negative lobe finalization calculations will follow.

Case 9: $CRV < -CRV_{thresh}$ and in a Negative Lobe.

Here, the current curvature value is below the dead-zone and the curvature signal is in a negative lobe. Thus, the negative lobe continuation calculations will follow.

In one embodiment, hysteresis is used to aid in identifying curvature lobes. After having started a lobe, one embodiment provides that the curvature value cross a threshold value closer to zero in order for the lobe to finish. Thus, hysteresis introduces another threshold value.

Consider next the metrics for characterizing each lobe according to the present subject matter. In one embodiment, those metrics include the total area of the lobe, the time of the lobe area centroid and the value of the original data at the time of the area centroid. In one embodiment, other metrics are used, including, for example, the peak curvature in the lobe, the time of the peak curvature, and the times of the lobe start and lobe finish.

Figure 6:
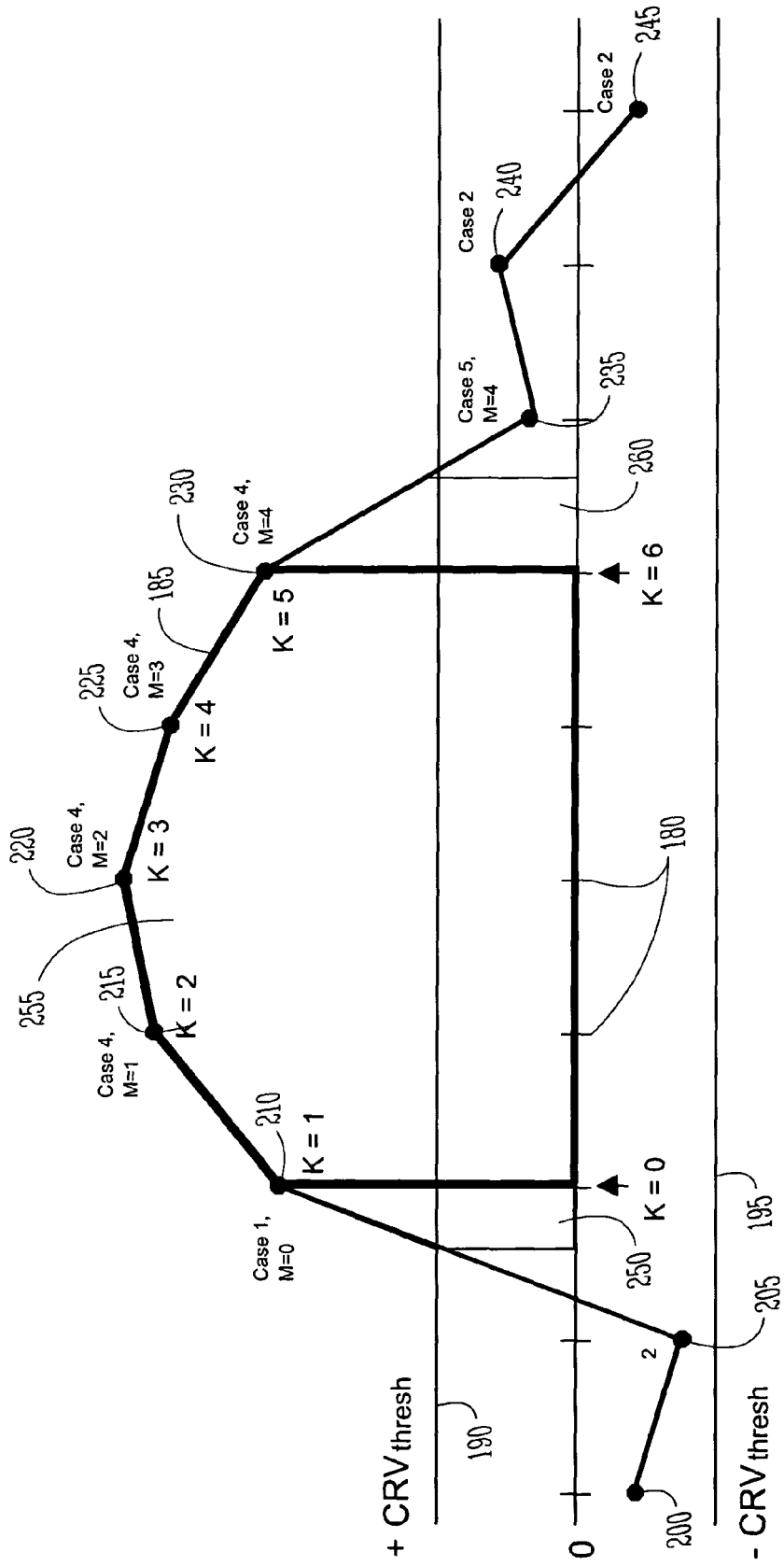
FIG. 6 graphically illustrates a method for determining area under a curvature lobe.

FIG. 6 shows an example of curvature lobe 185 as a series of calculated curvatures at each sample time. Tick marks 180 along the X axis represent the actual samples and thus are separated by ΔT. Zero curvature is shown as the X axis. The threshold curvature values, $+CRV_{thresh}$ 190 and $-CRV_{thresh}$ 195 are shown as horizontal lines above and below the X-axis. Curvature points 200-245 are shown as small solid circles.

As shown in the figure, initial curvature values at curvature points 200 and 205 are within the dead-zone of the threshold curvature values and thus, no lobe is yet established. Curvature point 210 is above the threshold and corresponds to Case 1 described above. The magnitude of initial area 250 is calculated as soon as the lobe is started according to case 1 described above. Upon determining curvature point 215, a contribution to the magnitude of main area 255 is calculated according to case 4 described above. In addition, the magnitude of main area 255 is increased with the determination of curvature points 220, 225, and 230. Upon determining curvature point 235 lying below $+CRV_{thresh}$ 190, the magnitude of final area 260 is calculated for the region below curvature lobe 185 and between curvature point 230 and the intersection with $+CRV_{thresh}$ 190. Curvature points 235, 240 and 245 lie in the dead-zone and do not contribute to an area calculation. The area of curvature lobe 185 is calculated to include the sum of initial area 250, main area 255 and final area 260.

In one embodiment, a value M of a counter is maintained by a processor to monitor sample-by-sample development of a lobe. When the 'start lobe' calculations are performed, the value for M is reset to zero and incremented with each subsequent point that remains outside the dead-zone. Values for M are illustrated at the different curvature points in FIG. 6.

To find the area under the curvature lobe, the value of M is set to zero and the initial area of a curvature lobe is computed as initial area=$(C_i+CRV_{thresh}) \cdot (C_i-CRV_{thresh})/(C_i-C_{i-1})$ when the lobe is started. For each successive curvature value, the value of M is incremented and the additional area contribution is computed as additional area=$-(M-1) \cdot C_i + M \cdot C_{i-1}$. When the lobe ends, the value of M is not incremented and the final area contribution is computed as final area=$M \cdot C_{i-1} + (C_i + CRV_{thresh}) \cdot (C_i - CRV_{thresh})/(C_i - C_{i-1})$. The sum of the initial, final, and all additional areas may then be multiplied by $\Delta T/2$ to find the area under the curvature lobe.

To find the first moment of the area under the curvature lobe, a similar approach is used. When the initial area of the curvature lobe is computed, the initial moment of the area is also computed as initial moment=$-\{C_1 + 2CRV_{thresh}\} \cdot \gamma^2$ where $\gamma=(CRV_{thresh}-C_{i-1})/(C_i-C_{i-1})$. For each successive curvature value in the lobe, an additional moment contribution is computed using the same M values as for the area computations. This additional moment contribution is computed as additional moment=$\{C_i \cdot (3M-1) + C_{i-1} \cdot (3M-2)\}$. When the lobe ends, a final moment contribution is computed at the same time that the final area is computed. The final moment is computed as final moment=$[CRV_{thresh} \cdot \{3M+2\gamma\} + C_{i-1} \cdot \{3M+\gamma\}] \cdot \gamma$.

The sum of the initial, final, and all additional moments may then be multiplied by $\Delta T^2/6$ to find the first moment of the area under the curvature lobe. The time of the centroid of the curvature lobe area is found by dividing the first moment of the curvature lobe area by the curvature lobe area as time=first moment of area/area. This time is with respect to the time of the curvature point that started the lobe.

For both the area and the first moment of the area, the calculations are constructed in such a way that the contribution of each curvature sample may be summed into a total area or total first moment of the area as the samples are collected. Thus, for all calculations, the factors include the present and previous curvature values, the threshold values, and the counter M. In this manner the area and the time of the centroid of the area are generated as soon as the lobe is ended.

In one embodiment, the present subject matter identifies characteristic points generated from point-by point processing of an input signal. In one embodiment, the characteristic points in the signal are detected and saved into a buffer. In one embodiment, each characteristic point is a set of values including the time of the characteristic point, the value of the input signal at that time, and a value describing the direction and extent of curve in the signal that produced the characteristic point.

Consider next a method of extracting characteristic points. In one embodiment, characteristic points of an electrocardiogram are extracted using a sampling at 400 Hz. In one embodiment, sampling is performed at 200 Hz. The sampled data is filtered using a 5-point (400 Hz) or 3-point (200 Hz) running average filter and a five least squares regression average-point curvature method to select characteristic points relating to the QRS complex.

For detecting curvatures associated with slower morphologies, sampling is at a slower rate, such as, for example, 50 Hz. An example of a wave having slower morphologies would be the T-wave in an electrocardiogram.

In one embodiment, multiple sampling rates are used for characteristic point extraction.

In one embodiment, dual-rate sampling is performed with sampling at 200 Hz providing fast characteristic points and sampling at 50 Hz providing slow characteristic points and a 3-point running average filter is used. Consider an example of dual-rate sampling using 200 Hz, yielding fast characteristic points, and 50 Hz, yielding slow characteristic points, with 5-point least squares regression size and 3-point running average filtering at both rates.

In one embodiment, curvature is found by using 5-point least squares regression filtering. The coefficients for finding the linear (Bi) and parabolic (Ci) fit coefficients in the cubic least squares regression to the data ($D_{i-2}$ to $D_{i+2}$) at the point i are as follows:

| Linear | Parabolic |
|---|---|
| $P_{-2} = (1/12) * \text{Rate}$ | $Q_{-2} = (10/70) * \text{Rate}^2$ |
| $P_{-1} = (-8/12) * \text{Rate}$ | $Q_{-1} = (-5/70) * \text{Rate}^2$ |
| $P_0 = 0$ | $Q_0 = (-10/70) * \text{Rate}^2$ |
| $P_1 = (8/12) * \text{Rate}$ | $Q_1 = (-5/70) * \text{Rate}^2$ |
| $P_2 = (-1/12) * \text{Rate}$ | $Q_2 = (10/70) * \text{Rate}^2$ | where Rate is the sampling rate in sample/sec, Bi is the sum of the products of these P least squares regression coefficients multiplied by the 5 corresponding data points centered on i ($D_{i-2}$ to $D_{i+2}$) and Ci is the sum using the Q least squares regression coefficients. Curvature is then computed as:

$$\text{Curvature} = \frac{2 \cdot Ci \cdot W}{[1 + \{Bi \cdot W\}^2]^{3/2}}.$$

where W is a constant. Since W appears in conjunction with fit coefficients Ci or Bi, the value can be incorporated into the computations as a data signal gain such that $D'(i) = W \cdot D(i)$. Then, the curvature expression becomes $$\text{Curvature} = \frac{2 \cdot C'i}{[1 + \{B'i\}^2]^{3/2}}.$$

where B'i and C'i are found using the D' data points rather than the D data points with the least squares regression coefficients.

The expression for curvature may then be rewritten as:

$$Curv' = \text{Curvature} \cdot Gn = \frac{C'i \cdot 2 \cdot Gn}{[1 + \{B'i\}^2]^{3/2}} = \frac{C''i}{[1 + \{B'i\}^2]^{3/2}}.$$

where Gn is an arbitrary value which is incorporated (with 2) into C''. If the curvature thresholds used for detection of characteristic points is adjusted accordingly, it does not matter whether point-by-point curvature or Gn times the point-by-point curvature is calculated. Incorporating the values $2 \cdot Gn$ into C''i can be accomplished by changing the least squares regression coefficients $Q_{-2}$ through $Q_2$ into new least squares regression coefficients ($Q'_{-2}$ through $Q'_2$) by multiplication with 2Gn. If Gn is selected as 7/(6 Rate) and the term Fn=Rate/12 is incorporated as additional data signal gain, then the least squares regression coefficients become:

| Linear | Parabolic |
|---|---|
| $P''_{-2} = 1$ | $Q''_{-2} = 4$ |
| $P''_{-1} = -8$ | $Q''_{-1} = -2$ |
| $P''_{0} = 0$ | $Q''_{0} = -4$ |
| $P''_{1} = 8$ | $Q''_{1} = -2$ |
| $P''_{2} = -1$ | $Q''_{2} = 4$ | with $D''(i)=2 \cdot W \cdot Fn \cdot D(i)$; and with $Ci''=Q''_{-2} \cdot D''(i-2)+Q''_{-1} \cdot D''(i-1)+Q''_{0} \cdot D''(i)+Q''_{+1} \cdot D''(i+1)+Q''_{+2} \cdot D''(i+2)$; and with $Bi''=P''_{-2} \cdot D''(i-2)+P''_{-1} \cdot D''(i-1)+P''_{0} \cdot D''(i)+P''_{-1} \cdot D''(i+1)+P''_{+2} \cdot D''(i+2)$.

Note that the coefficients are all powers of two (either 0, 1, 2, 4 or 8), thus simplifying hardware or firmware implementation of the present subject matter.

When using two sample rates for determining characteristic points, the computed curvatures will be different when computed at different rates. Thus, two threshold levels and parallel sets of computations are used. Also, the running average filtering is different with the fast rate filtering using five consecutive points while the slow rate filtering uses every fourth point spaced over sixteen points.

In one embodiment, the linearity of the least squares regression operation is used. The running average filtering operation are performed at the fit coefficient level (i.e. the Bs and Cs) rather than the data level. In this embodiment, two filtering operations are performed (one for Bs, one for Cs) at each rate.

In one embodiment, the fast and the slow running average filtering operations are performed in parallel.

In one embodiment, the following method is used to select the values for the characteristic points.

Starting at the time of one sample, the sensing hardware and software of the present subject matter begins acquiring the next sample so that the actual sample reflects the nature of the signal between the last sample and the current sample. At the actual time of the sample, the value of the sample may be ascribed to the time half-way between the current sample and the previous sample. Samples at the slow sample rate apply to the signal two fast sample steps earlier than the actual sample time.

In one embodiment, a circular data buffer is used. Data is acquired at the fast sample rate and used to fill a circular data buffer. Once the timing of a fast or slow characteristic point is determined, the data value for that characteristic point is found from the data stored in the circular buffer. Thus, the data buffer is sized so that the requisite data is still available in the buffer. In one embodiment, the buffer is sized to hold about 500 millisecond of data or 256 data points. In one embodiment, the circular buffer is implemented as a memory array with an index pointer. In one embodiment, the index pointer includes a binary counter and the buffer size is a power of two.

In one embodiment, running average filtering (RAF) is performed on the input data. In various embodiments, the filtering is provided by a circular buffer or a shift register set. The values in the circular data buffer reflect the fast running average filtering. In one embodiment, a hybrid approach is used where the fast running average filtering is performed and then the data is placed into a circular buffer.

In one embodiment, running average filtering reduces curvature noise relative to the signal content of fast curvature signals. An electrocardiogram signal typically takes relatively large excursions away from zero curvature at the times of fast turns in the signal. However, when the fast turns are less severe, the curvature signal does not move as far away from zero and curvature noise can prematurely end the curve lobe. The result is that one small curvature lobe is broken into two or more even smaller lobes. Thus, in one embodiment, the curvature noise relative to the signal content is reduced, for fast curvature signals, by running average filtering.

Filtering of the input signal does not achieve the same effect as filtering the actual curvature signals. In one embodiment, 3-point running average filtering is applied to the fast curvature values.

In one embodiment, fast curvature values are computed as average point curvature and 3-point running average filtering of the curvatures so that the fast curvature value computed when the current sample is taken applies to a time in the input signal that is five time steps earlier than the current sample.

In one embodiment, slow curvature values are computed at ¼ the fast sample rate and are computed as average-point curvatures so that when the every fourth fast sample is taken, slow curvature is computed and it applies at a time in the input signal that is four slow (sixteen fast) time steps earlier than the current sample.

In one embodiment, the detection of a curvature lobe and characteristic points entails both fast and slow characteristic point detection performed in parallel. In one embodiment, separate curvature thresholds and curvature area thresholds are used for the fast and slow operations.

In one embodiment, a curvature lobe is ended when the curvature signal crosses the same threshold used to start the lobe but in the opposite direction of the crossing that started the lobe. In one embodiment, a hysteresis is used so that a curvature lobe is ended when the curvature signal crosses a threshold that is smaller (i.e. closer to zero) than the threshold used to start the lobe but in the opposite direction of the crowing that started the lobe. In one embodiment, a curvature lobe is ended when the curvature signal crosses zero as the hysteresis value.

In one embodiment, the value of W is selected according to the following procedure. Select an approximate range for W from the following analysis. At a 200 Hz sampling rate, the QRS takes approximately five samples. The signal at the peak is approximated by 128. If the QRS were to be approximated (in curvature space) as a semicircle arching from zero to the peak then back to zero in five points, then the radius of that semicircle would be 0.01 sec and the peak would have a value of 0.01. Thus, the value of W would be the one that, when multiplied, the peak (128) would have the value of 0.01, i.e. $W=0.01/128=0.000078$. In one embodiment, $W=0.000122=1/8192$ which is a power of two.

Consider selection of curvature threshold values for characteristic point detection. Thresholds, in one embodiment, reduce or eliminate the noise characteristic points and computational burden. This noise is the natural results of the curvature signal hovering around zero (or some other value) when the raw signal does not otherwise have characteristic turnings.

In one embodiment, for a curvature lobe to be detected, the point-wise curvature falls outside of a dead-band formed by the threshold values on either side of zero. Reducing this threshold towards zero increases the number of curvature lobes that are detected and increases the computational burden. In one embodiment, a threshold value is selected by using approximately a 1 minute epoch of the input signal to make a histogram of the fast curvature values computed at each sample time. The threshold value is selected as one which corresponds to 20% of the peak. This value is then used as the threshold for both the fast curvature and slow curvature feature selection process.

In one embodiment, the noise lobes are removed by requiring that a detected lobe must exceed a critical area limit. The noise lobes have generally small areas while the real lobes associated with characteristic turns in the signal usually have substantial areas.

In one embodiment, different values are used for the fast curvature and slow curvature area thresholds. Using the number of beats occurring in the one minute epoch used to set the gain and curvature thresholds, select a desired number of fast and slow characteristic points to find for these beats. For example, in one embodiment, five fast characteristic points per beat and eight slow characteristic point per beat are used as targets. The area thresholds are then adjusted until these target numbers of characteristic points are found. In one embodiment, a lower area limit of 0.1 is used.

In one embodiment, a template is established for classifying beats. For example, a characteristic point template includes a rectangular box covering a time (relative to a fiducial characteristic point) and signal amplitude. The template also includes a curvature area sign.

Rate Estimation

Heart rate, expressed in units of beats per minute, can be determined without relying on detection of individual beats. Mathematically, the heart rate is determined by the number of characteristic points per minute divided by the number characteristic points per beat. The calculation of the number of characteristic points per minute is straightforward. An autocorrelation function is evaluated to determine the number characteristic points per beat.

In one embodiment, the number of characteristic points per beat is calculated by performing the autocorrelation function in the time domain. In one embodiment, the number of characteristic points per beat is calculated by performing the autocorrelation function in the characteristic point domain.

In the series, or stream, of characteristic points describing the input signal, let the individual characteristic points be denoted as $CP_1, CP_2, CP_3, \ldots, CP_n$. Each characteristic point has a time value, an area (turn area) value and a voltage value, and for the $i^{th}$ characteristic point, these are denoted as $CP_{i\,T}$, $CP_{i\,A}$ and $CP_{i\,V}$, respectively.

The values for the autocorrelations range between +1 and −1. The shift index (k) for the autocorrelations denotes the shift in the characteristic point domain. For example, at k=0, there is no shift and at k=1, the characteristic points are shifted by one.

In one embodiment, the autocorrelation of characteristic points in the characteristic point domain entails, for each value of the shift index k, multiplying like metrics of corresponding characteristic points and summing to produce a value. For example, when k=3, the value of the series includes the sum of the product of $CP_{1V}$ and $CP_{4V}$, $CP_{2V}$ and $CP_{5V}$, $CP_{3V}$ and $CP_{6V}$ and so on.

Figure 7:
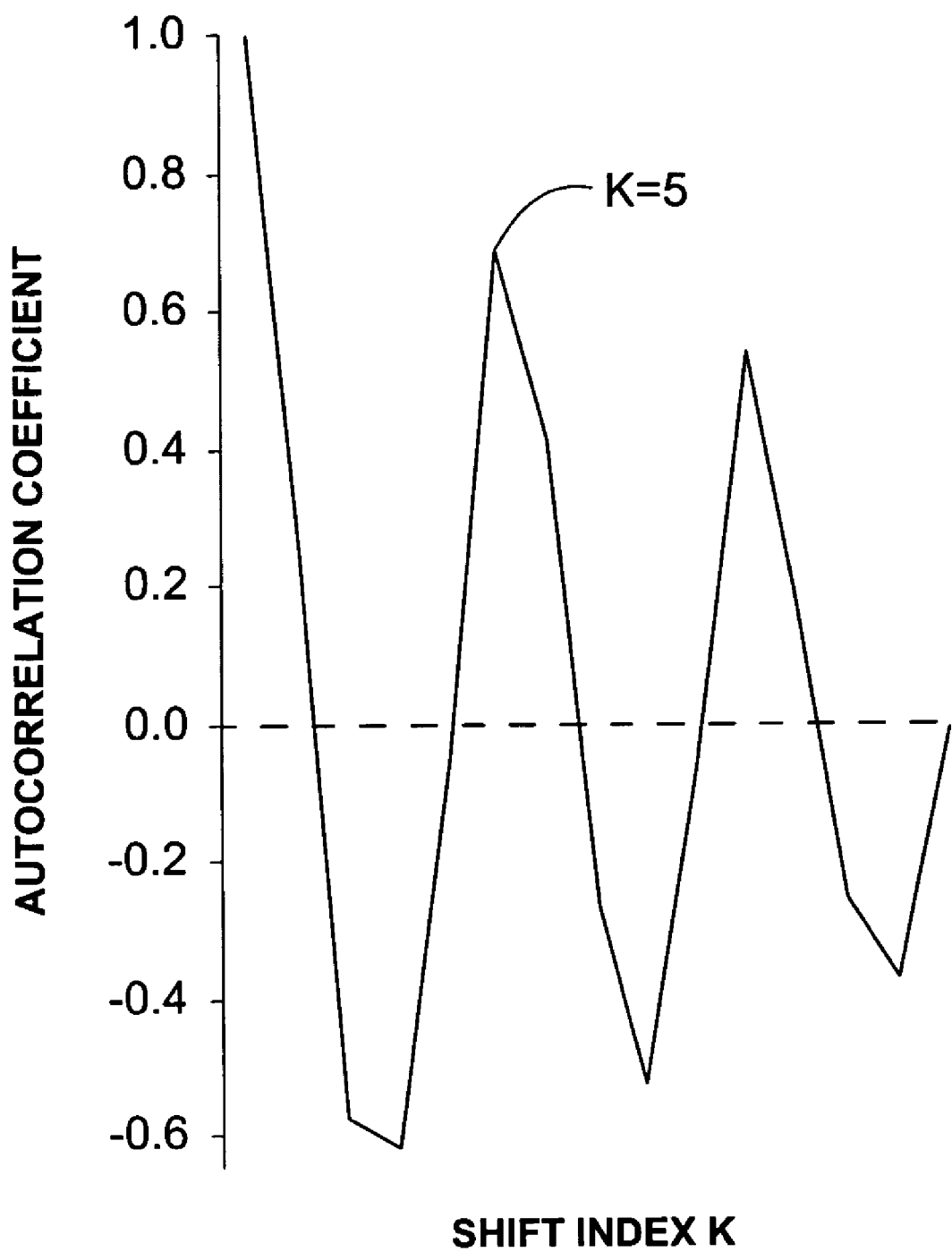
FIG. 7 illustrates a characteristic point domain autocorrelation plot of characteristic points according to one embodiment of the present subject matter.

The results are graphically depicted in the autocorrelation plot of FIG. 7. In the figure, the vertical axis is an autocorrelation coefficient based on an autocovariance function divided by a variance function and the horizontal axis is the shift index k. The plot in the figure has a peak at a shift index of five which indicates that on average, each beat is represented with five characteristic points.

Using exemplary data collected over an epoch having a duration of 6.288 seconds, a total of 80 characteristic points were generated for a rate of 12.722 characteristic points per second. With five characteristic points per beat, the heart rate is calculated as 152.67 beats per minute.

In one embodiment, an autocorrelation is performed using the time differences between successive characteristic points. For example the difference in time for adjacent characteristic points can be expressed as $CP_{i\,DT}=CP_{i\,T}-CP_{i-1\,T}$. In addition, the difference in area for adjacent characteristic points can be expressed as $CP_{iDA}=CP_{i\,A}-CP_{i-1\,A}$ and the difference in voltage can be expressed as $CP_{i\,DV}=CP_{i\,V}-CP_{i-1\,V}$.

In various embodiments, the difference functions $CP_{i\,DT}$, $CP_{i\,DA}$ and $CP_{i\,DV}$ are autocorrelated to determine the number of characteristic points per beat. In various embodiments, $CP_{iA}$, $CP_{iV}$, $CP_{iDT}$, $CP_{iDA}$, and $CP_{iDV}$ are autocorrelated, either alone or in combination (for example, the product $CP_{iV} \times CP_{iDT}-CP_{iA}$), to determine the number of characteristic points per beat.

By way of example, an autocorrelation of the characteristic point voltage values in the characteristic point domain can be expressed as:

$$A_V(k) = \sum_{i=1}^{i=N}(CP_{iV} - CP_{iV\,AVG})(CP_{i+kV} - CP_{iV\,AVG}) \Big/ \sum_{i=1}^{i=N}(CP_{iV} - CP_{iV\,AVG})^2$$

where N is the number of characteristic points, $CP_{iV\,AVG}$ is the average value of the N characteristic point values and k is the index in the characteristic point domain.

In one embodiment, heart rate is found from the autocorrelation of characteristic points in the time domain. In one embodiment, the cardiac signal is reconstructed for autocorrelation from the series of characteristic points. In one embodiment, the reconstruction produces evenly spaced samples for the autocorrelation. In one embodiment, the reconstruction and autocorrelation are performed in closed form using the characteristic point voltages and times from the series of characteristic points.

In one embodiment, only timing information for the characteristic points in the cardiac signal are used for the autocorrelation. In one embodiment, a time difference between successive characteristic point times in the series of characteristic points versus the time of each characteristic point in the series forms a time difference function. In one embodiment, the time difference function is constructed to have evenly spaced samples for autocorrelation. In one embodiment, the autocorrelation of the time difference function is performed in closed form using only the characteristic point times from the series of characteristic points. In general, the first peak of the autocorrelation is equal to the reciprocal of the heart rate.

Figure 8A:
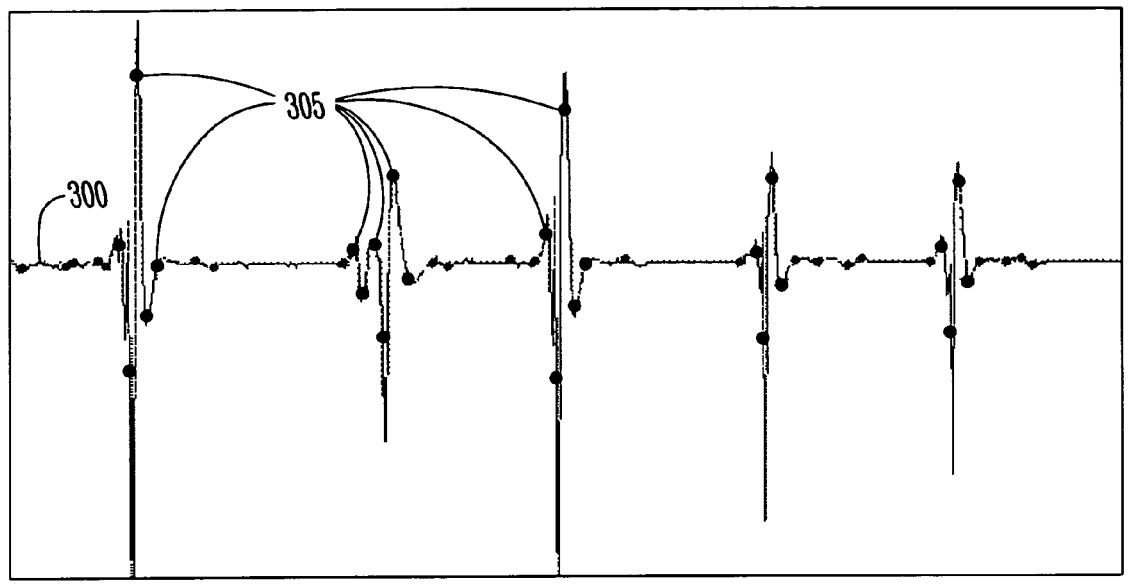
FIGS. 8A, 8B, 8C, 8D, 8E and 8F illustrate a method to form a characteristic point time difference function according to one embodiment of the present subject matter and the resulting time domain autocorrelation.
Figure 8B:
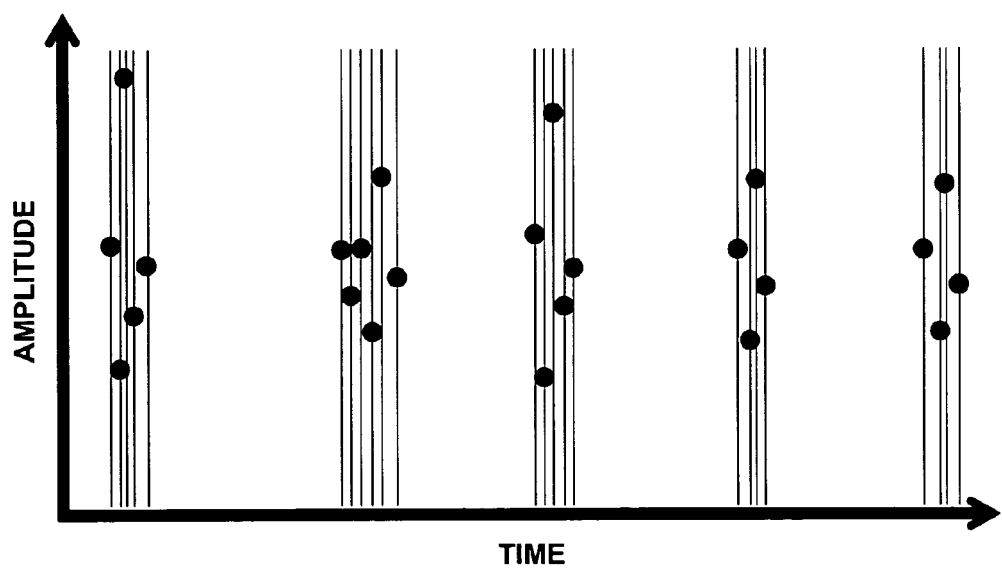
Figure 8C:
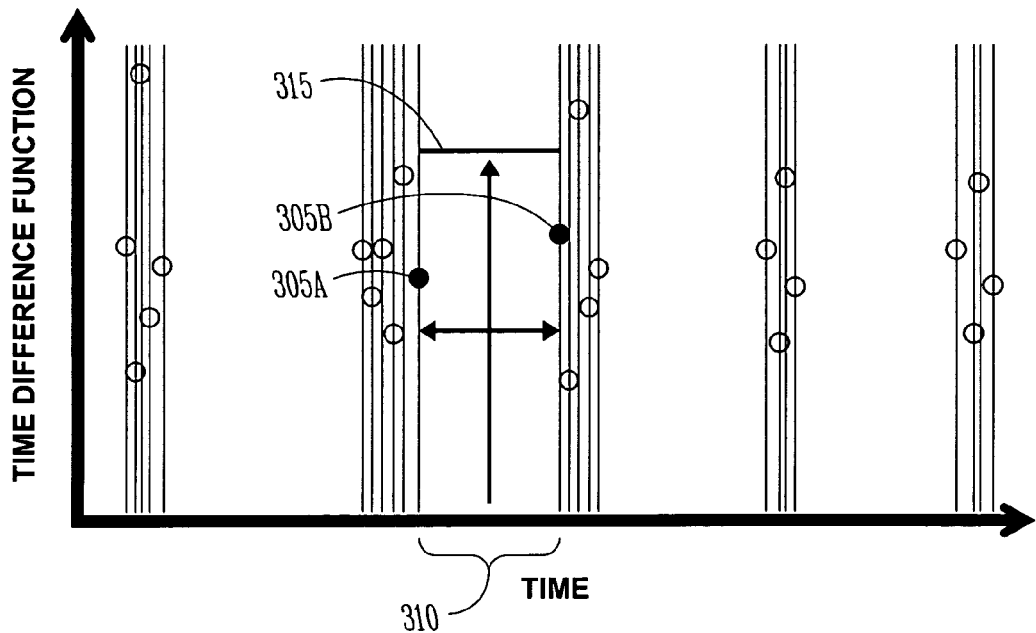
Figure 8D:
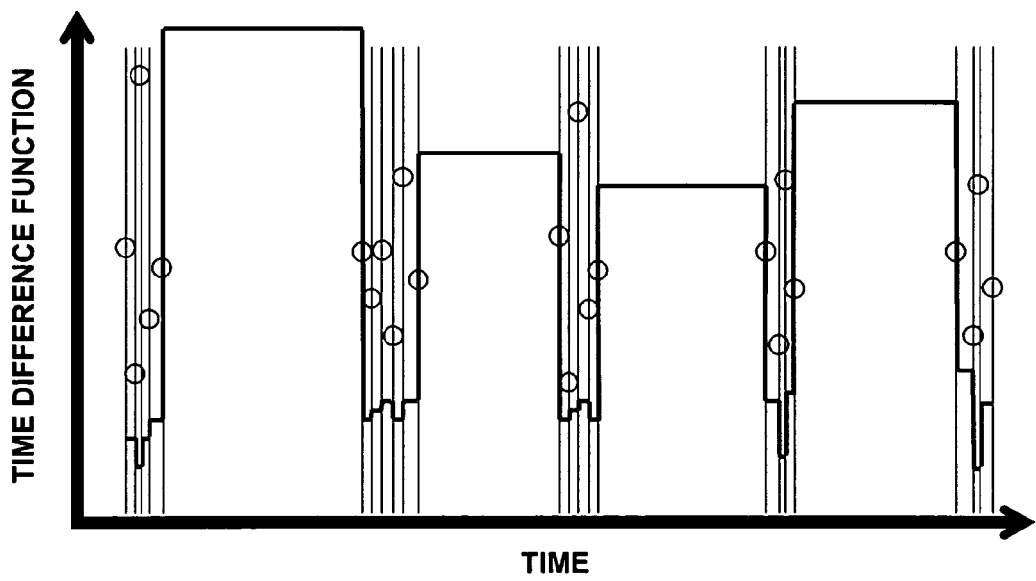
Figure 8E:
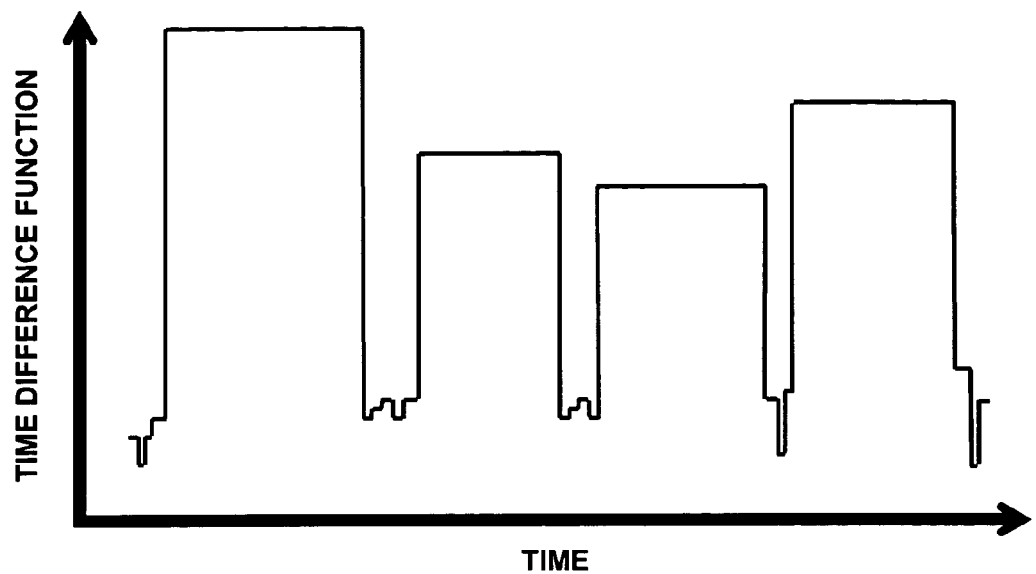
Figure 8F:
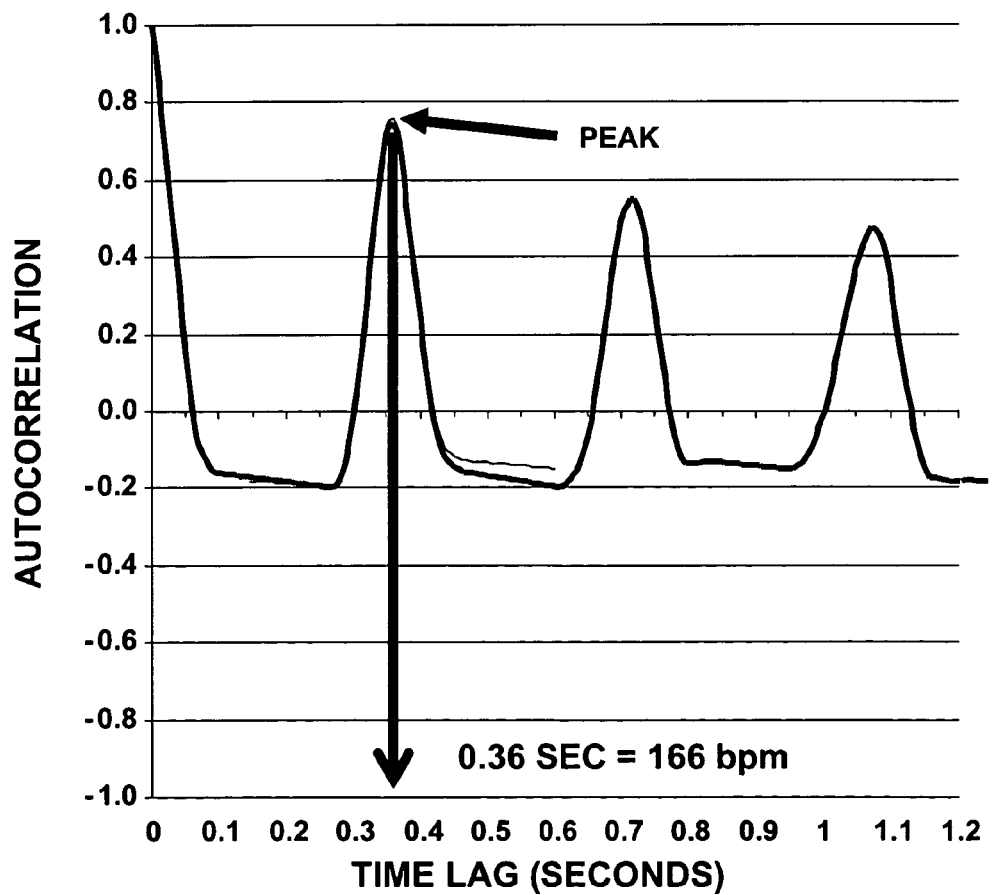

FIG. 8A illustrates a selected epoch of cardiac signal 300 having characteristic points 305 marked thereon. The epoch includes five heart beats, each having between four and six characteristic points. FIG. 8B illustrates the amplitude of the signal, at each characteristic point, as a function of time. FIGS. 8C and 8D illustrate the time differences between successive characteristic points in the series of characteristic points. When plotted against the times of the characteristic points, these form a time difference function which may then be autocorrelated. In FIG. 8C, the time difference 310 between adjacent characteristic points 305A and 305B is transformed to an amplitude denoted by the horizontal line 315. Thus, the time difference function between points 305A and 305B is equal to this line segment 315. FIG. 8D illustrates the time differences for all characteristic points in the epoch. FIG. 8E illustrates the time difference after having removed the characteristic points. The waveform shown in FIG. 8E is depicted as an autocorrelation plot in FIG. 8F which shows that the first peak occurs at time 0.360 seconds which corresponds to a beat rate of 166 bpm.

In one embodiment, heart rate is found from the estimated number of characteristic points per beat and the times of the characteristic points in the series of characteristic points. In one embodiment, an average interval representing one beat is found and the interval is the reciprocal of the heart rate for the rhythm. For example, if the estimate for the number of characteristic points per beat is 5, then the average time interval between each pair of characteristic points that are 5 characteristic points apart is used to find an average time interval for the rhythm as follows:

$$\text{Average Interval} = \sum_{i=K_P}^{i=N} (CP_{iT} - CP_{i-K_pT})$$

where Kp is the estimated number of characteristic points per beat.

Other autocorrelations are also contemplated. For example, in various embodiments, the characteristic point voltage values and area values are autocorrelated.

Sub-harmonics in the autocorrelation function can be used to determine the heart rate. The sub-harmonic frequencies are multiples of the fundamental frequency of the heart rate. For example, if the underlying rhythm is a monomorphic ventricular tachycardia (MVT), then the same basic beat shape is repeated at regular intervals. In the characteristic point domain, this means that the autocorrelation plot will have multiple peaks. For example, an autocorrelation plot for a MVT rhythm exhibits a peak at a shift index of 5 as well as the sub-harmonics corresponding to the shift index at 10, 15, and 20.

Figure 9:
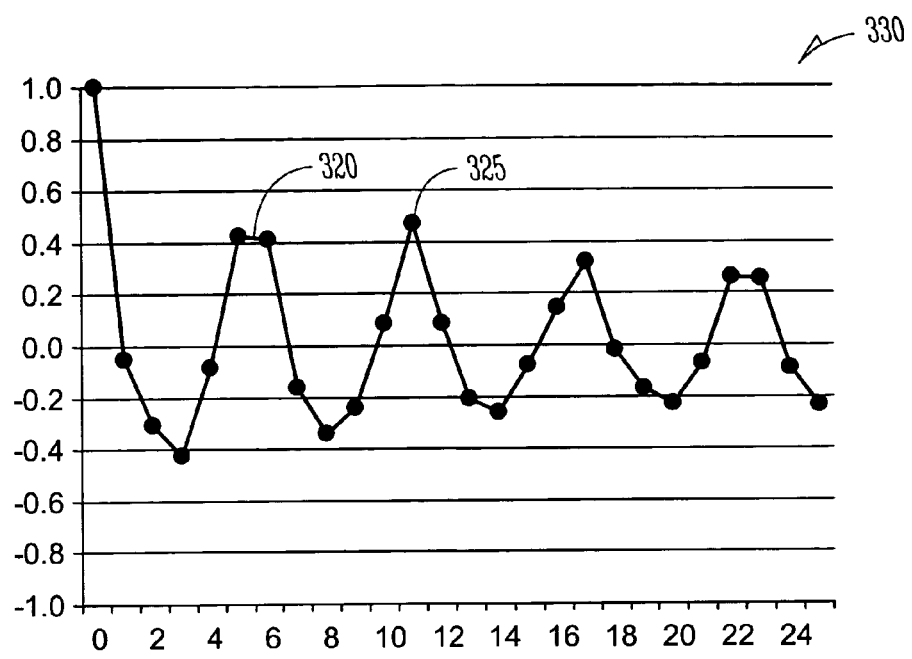
FIG. 9 illustrates a characteristic point domain autocorrelation plot derived from a series of characteristic point.

In one embodiment, the sub-harmonics are used to find the rate. In plot 330 of FIG. 9, exemplary autocorrelations for DT are illustrated. The autocorrelations in the figure are derived from a particular cardiac epoch. In plot 330, it is not clear if first peak 320 for the corresponding atrial cardiac epoch is at k=5 or k=6. The location of second peak 325, derived from the first sub-harmonic, can resolve the ambiguity.

Figure 10:
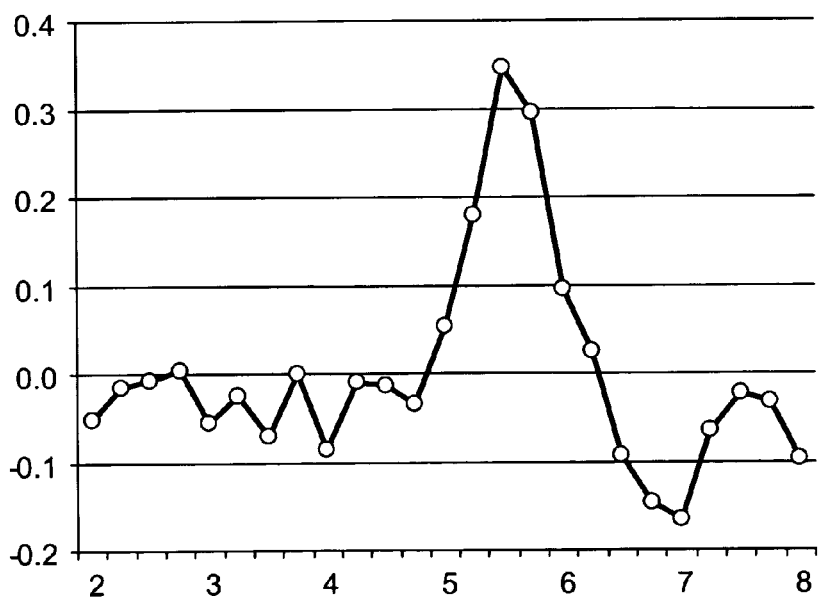
FIG. 10 illustrates fraction peaks in characteristic point domain from sub-harmonics.

In one embodiment, a method to process the autocorrelation provides an improved resolution to find the peaks by incorporating sub-harmonics. As in FIG. 9, the autocorrelation has values at k=1, k=2, etc. Initially, additional points are added to the autocorrelation by adding points at ¼ step resolution. For instance, in FIG. 9, additional points are added at 2.25, 2.5, 2.75, 3.25, 3.5, 3.75, and so forth. The autocorrelation values for these additional points are found by interpolating between the original points. Next, a sub-harmonic autocorrelation is found by averaging the values at harmonics. For example, at k=2, the value for the sub-harmonic autocorrelation is found by averaging the points at 2, 4, 6 etc. of the autocorrelation. At the point k=2.25, the value for the sub-harmonic autocorrelation is found by averaging the points at k=2.25, 4.5, 6.75, etc. of the autocorrelation. FIG. 10 illustrates an example of the sub-harmonic autocorrelation from FIG. 9. In FIG. 10, the peak is now more clearly at k=5.5 which is between the steps k=5 and k=6 of the original correlation. In one embodiment, the averages of the first three sub-harmonics are used in to form the sub-harmonic autocorrelation. In one embodiment, the peak of the sub-harmonic autocorrelation is used to estimate the rate of the rhythm.

Autocorrelation in the time domain can be used for identifying periodicity in a signal. Periodicity can also be identified by performing the time domain autocorrelation of the voltage signal using the characteristic points voltage values. In one embodiment, the time domain signal is represented by straight line segments connecting consecutive characteristic points. The line segment representation of the signal is then autocorrelated using integration of line segments. The endpoints of the line segments are the characteristic points, and thus, the calculations are simplified.

For example, consider a signal described by N characteristic points, where $CP_1$ is the oldest characteristic point, $CP_2$ is the next oldest and so on. A closed form autocorrelation for a given time-lag Q is then computed by sliding each line segment by Q and then integrating (for that line segment) the product of that line segment and the portion of the signal with which it overlaps. The values are obtained for all line segments to find the autocorrelation for the time-lag Q. The same operation is then performed for other values of time-lag to find the time domain autocorrelation (autocorrelation vs. time-lag).

Figure 11:
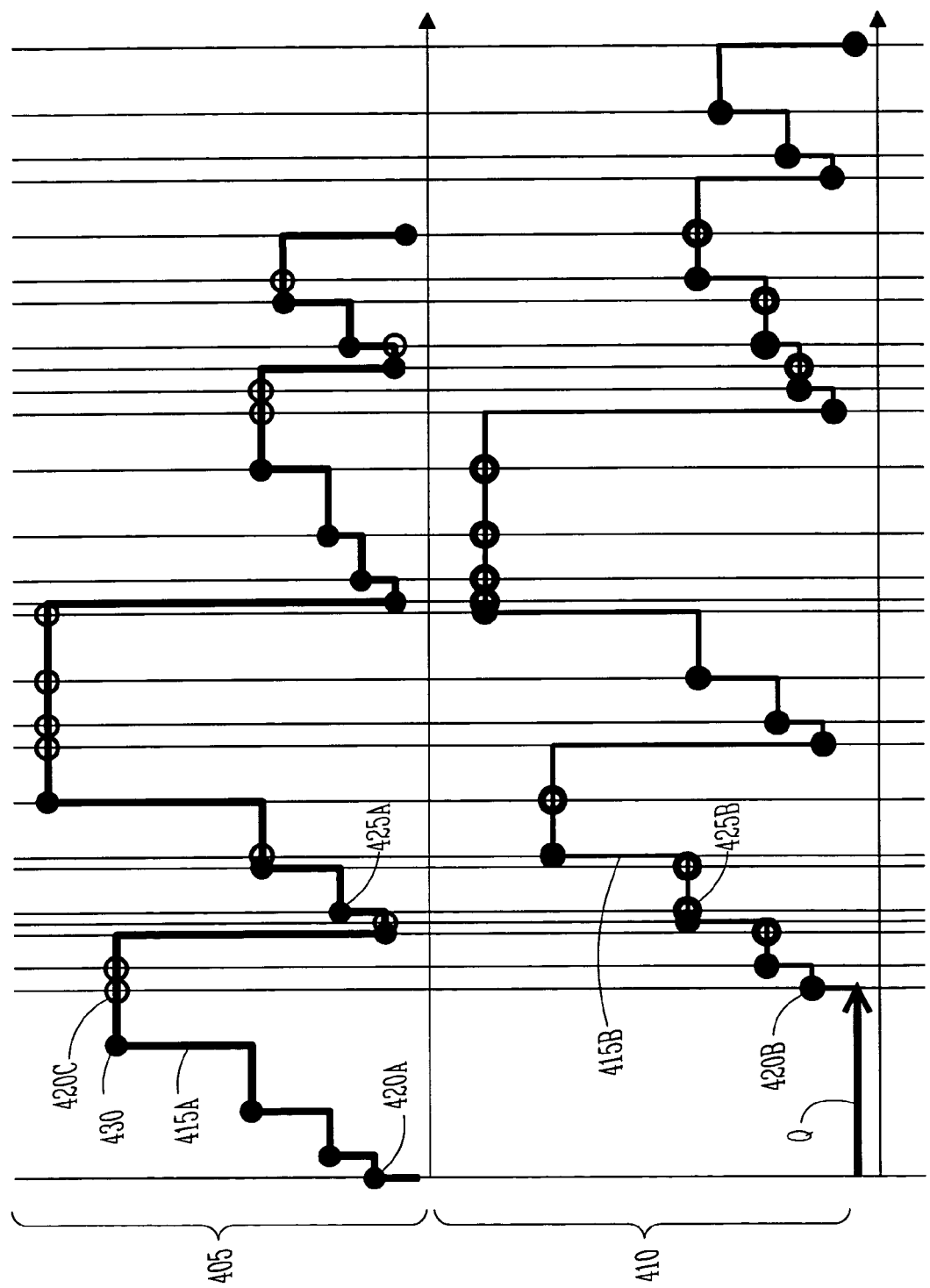
FIG. 11 illustrates a time function that represents intervals between characteristic points before and after a time shift.

The heart rate can also be determined by autocorrelating a function of the characteristic points in the time domain. For example, in one embodiment, a closed form autocorrelation is calculated, as shown in FIG. 11.

Consider a sequence of characteristic point time differences $CP_{i,T}$ where there are N characteristic points. Time difference function 415A is established and has a value, at each characteristic point, equal to the time interval between $CP_i$ and $CP_{i+1}$ as shown with the heavy black line and solid black circles in chart 405. Time function 415A is shifted in time by Q as represented as 415B in chart 410. Each point along the shifted function 415B now falls onto some point of the un-shifted function 415A. For example, point 420B (derived from shifted point 420A) on chart 410, is projected onto point 420C on chart 405. Similarly, the values of the un-shifted function projects onto the time-shifted function. For example, point 425A of chart 405 projects to point 425B of chart 410. The autocorrelation of this function in the time domain is found by determining the area under the product of the curves which is equivalent to adding the area contribution for each portion between the line vertical lines shown in FIG. 11.

Next, consider the shifted curve 415B on chart 410. Each segment between the vertical lines is bounded in time by either a shifted or un-shifted characteristic point. Further, these bounding endpoints have a value equal to either the shifted value or the un-shifted value respectively. Each segment also aligns with a second set of values (shown in chart 405) as either un-shifted (solid circles) or shifted (open circles) values. The values for the open circles (chart 405) or open circles (chart 410) are found by shifting the characteristic points either forward (chart 405) or backwards (chart 410) in time. In one embodiment, the calculation of area is found from the shifted line segments, and the corresponding un-shifted line segments. For example, the line segment between 420B and the next point on the shifted function 415B falls entirely on the same line segment after point 430 of the un-shifted function 415A. The values for 420B and 430 are known. Because 415B is a time difference function, the duration after 420B until the next point is also the value of 420B. Thus, the contribution to the autocorrelation integral for this line segment is equal to the value of point 420B squared times the value of the point 430. The autocorrelation is the sum of all line segments.

The time domain autocorrelation of the characteristic points time difference function can be used for estimating rate. Various methods are used to estimate the rate. In some methods, the autocorrelation between 0.15 sec and 0.6 seconds time lag is fit with a straight line via least squares regression and this trend-line is removed from the autocorrelation data in this same range. In one method, a point-by-point scan of the de-trended autocorrelation is performed to find all local peaks. Each local peak, is only then considered if it is faster than the first sub-harmonic of the first such peak. For example, if the first peak in the autocorrelation represents a rate of 300 bpm, then peaks less than or equal to 150 bpm are not considered. All of the peaks remaining in consideration have a specific lag time and an autocorrelation value. In one embodiment, the autocorrelation values are used to weight the rates associated with those peaks to find an average rate for the rhythm.

In one method, the value of the de-trended autocorrelation function in the range from 0.15 to 0.6 seconds time lag and above zero are used to find an average time lag as SUM (corr*lag)/sum(corr). The average time lag is used to find the rate. In this method, the product of each de-trended autocorrelation value that is between 0.15 seconds and 0.6 seconds and greater than zero is multiplied by the corresponding time-lag and summed to find SUM(corr*lag). Also, the de-trended autocorrelation values that meet these criteria are themselves summed to find SUM(corr).

In one embodiment, the average autocorrelation value associated with the peak is used to find the rate.

Other methods are also contemplated for finding the heart rate.

Rhythm Discrimination

In one embodiment, analysis of characteristic points is used to discriminate among different rhythm types.

Rhythm types are associated with a relationship between an atrial cardiac signal and a ventricular cardiac signal. Thus, to discriminate among different types, an atrial input signal and a ventricular input signal are used to generate a series of atrial characteristic points and a series of ventricular characteristic points. In various embodiments, the rhythm can be discriminated by estimating the variation in characteristic point timing and cross-correlations in the characteristic domain. In one embodiment, the relative timing of characteristic points in the atrial and ventricular rate channels is used to discriminate.

In one embodiment, the individual characteristic points in the atrial channel are compared with those in the ventricular channel.

In one embodiment, a time window is established in advance of each ventricular characteristic point. For an appropriately sized window, a characteristic point in the ventricular complex should have one or more atrial characteristic points within the window. Each ventricular characteristic point is considered individually and the number of atrial characteristic points that are contained in such a window is determined. In one embodiment, a constraint requires that each atrial characteristic point is counted only once. This count is referred to as a forward count and is denoted A:V and is equal to the number of atrial characteristic points which fall in a time window of one or more ventricular characteristic point.

The dimensions of the time window are selected to yield accurate rhythm discrimination results. In one embodiment, the time window is located between 300 milliseconds and 100 milliseconds before a ventricular characteristic point. In one embodiment, the time window is located between 250 milliseconds and 150 milliseconds before a ventricular characteristic point. Other dimensions are also contemplated. In one embodiment, the time window dimensions are selectable based on manual inputs or automatically based on a measured or calculated parameter. In one embodiment, a window dimension is remotely selected and communicated to an implantable device.

Consider the resulting count, for a simple conducted rhythm where each atrial depolarization corresponds with a ventricular depolarization after some delay. In such a case, most of the atrial characteristic points will be counted so that the ratio of counted atrial characteristic points to the total number of atrial characteristic points (denoted as $A_{cnt}$) will be nearly unity.

In one embodiment, far-field sensing of ventricular depolarizations on the atrial channel may cause additional characteristic points in the atrial channel but these additional characteristic points would generally be simultaneous or later than the ventricular characteristic points so would not fall inside the windows.

If the heart is beating in atrial fibrillation (A-fib), rather than a one-to-one conducted rhythm, then the total atrial characteristic points count will be larger. Also, a smaller percentage of atrial characteristic points, will fall into a ventricular characteristic point window since not all atrial complexes would be conducted and lead to a ventricular complex. Thus, the ratio should become smaller.

If the heart is beating in MVT, polymorphic ventricular tachycardia (PVT) or ventricular fibrillation (VF), then the total number of atrial characteristic points would not increase but a smaller number of characteristic points would be associated with a ventricular characteristic point time window because of the loss of A-V synchrony. On the other hand, more ventricular characteristic points would be present to increase the A:V number. Accordingly, the ratio is unlikely to be greatly affected.

Next, consider the same timings from the point of view of the ventricular characteristic points. Each ventricular characteristic point is analyzed and a count is made of the number of ventricular characteristic points that have at least one atrial characteristic point within a time window for the ventricular characteristic point. This count is referred to as a backward count and is denoted V:A and is equal to the number of ventricular characteristic points which have one or more atrial characteristic points in the advance time window.

For a one-to-one conducted rhythm, most of the ventricular characteristic points will meet the criteria so that the ratio of counted ventricular characteristic points to the total number of ventricular characteristic points ($V_{cnt}$) will be nearly unity.

If the heart rhythm was actually A-fib instead of a one-to-one conducted rhythm, then the total number of ventricular characteristic points would be greater reflecting an elevated rate. However, since each ventricular complex would be from a conducted atrial complex, the percentage of ventricular characteristic points that are associated with atrial characteristic points would remain about the same even though there are more ventricular characteristic points.

If the actual rhythm was an MVT or PVT/VF, then the total number of ventricular characteristic points would increase and a smaller number would be associated with an atrial characteristic point in their time window. Accordingly, the ratio would also be reduced.

The ventricular and atrial characteristic points are found over the selected epoch. If the rhythm is one-to-one conduction, then there is the same number of beats in each channel. Without knowing the number of beats in the epoch, an estimate can be made for the number of atrial characteristic points per beat relative to the number of ventricular characteristic points per beat, denoted here as $A_{cnt}/V_{cnt}$.

If the rhythm is one-to-one, then the percentage of atrial characteristic points associated with ventricular characteristic points should approximate the percentage of ventricular characteristic points associated with atrial characteristic points, however, the number of characteristic points per beat may be different in the two channels.

In various embodiments, the value $V:A/V_{cnt}$ or the value $[(A:V/A_{cnt})/(V:A/V_{cnt})]/[A_{cnt}/V_{cnt}]$, which can be rewritten as $(V_{cnt}/A_{cnt})^2/(A:V*V/A)$, is used to discriminate among rhythms.

Figure 12:
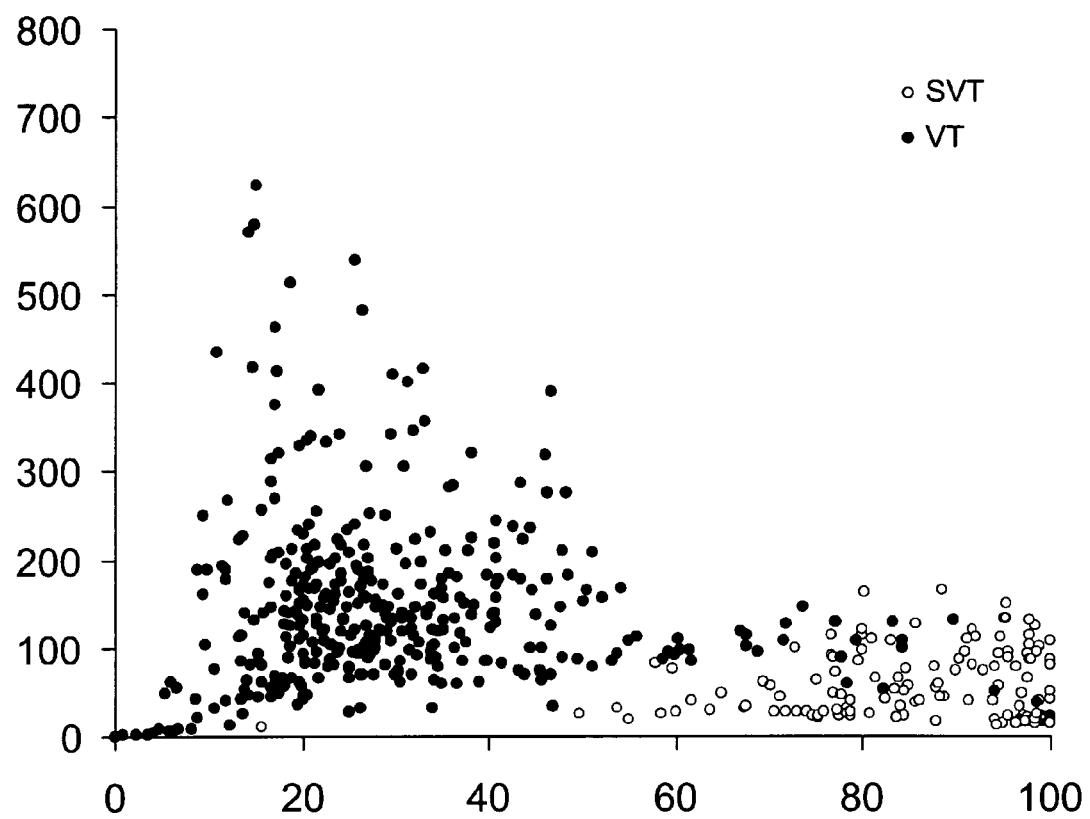
FIG. 12 illustrates an X-Y plane corresponding to a time relationship between atrial characteristic points and ventricular characteristic points for selected rhythm types.

In one embodiment, a plot is generated to graphically illustrate the relationship between atrial characteristic points and ventricular characteristic points. In FIG. 12, a plot is shown for approximately 500 rhythms that had either supra-ventricular origin (SVT) or ventricular origin (VT). The X, or horizontal axis is $100*(V:A/V_{cnt})$ and the Y, or vertical axis is $100*(A:V*V_{cnt}/A_{cnt}^2)$.

The different regions of the X-Y plane correspond to the different rhythm types. For example, the SVT rhythms fall generally in the range below about 150 on the Y-axis and between 50 to 100 on the X-axis. In contrast, VT rhythms generally fall much closer to zero on the X-axis reflecting the expected strong decrease of $V:A/V_{cnt}$. Furthermore, the VT rhythms fall higher on the Y-axis since $V_{cnt}$ is generally higher.

In one embodiment, an X and Y value for a rhythm is found by processing the timings of the atrial and ventricular characteristic points according to the present subject matter. In one embodiment, the position of the X and Y values on the plot is used for classifying the rhythm. In one embodiment, the classification is between either SVT or VT. In one embodiment, the classification is made by comparing the X-Y point with fixed boundaries on the plot. In one embodiment, the boundaries are comprised of one or more straight line segments. In one embodiment, the rhythm is classified as SVT if the X-Y point falls on one side of the boundary and is classified as VT if it falls on the opposite side of the boundary.

Figure 13:
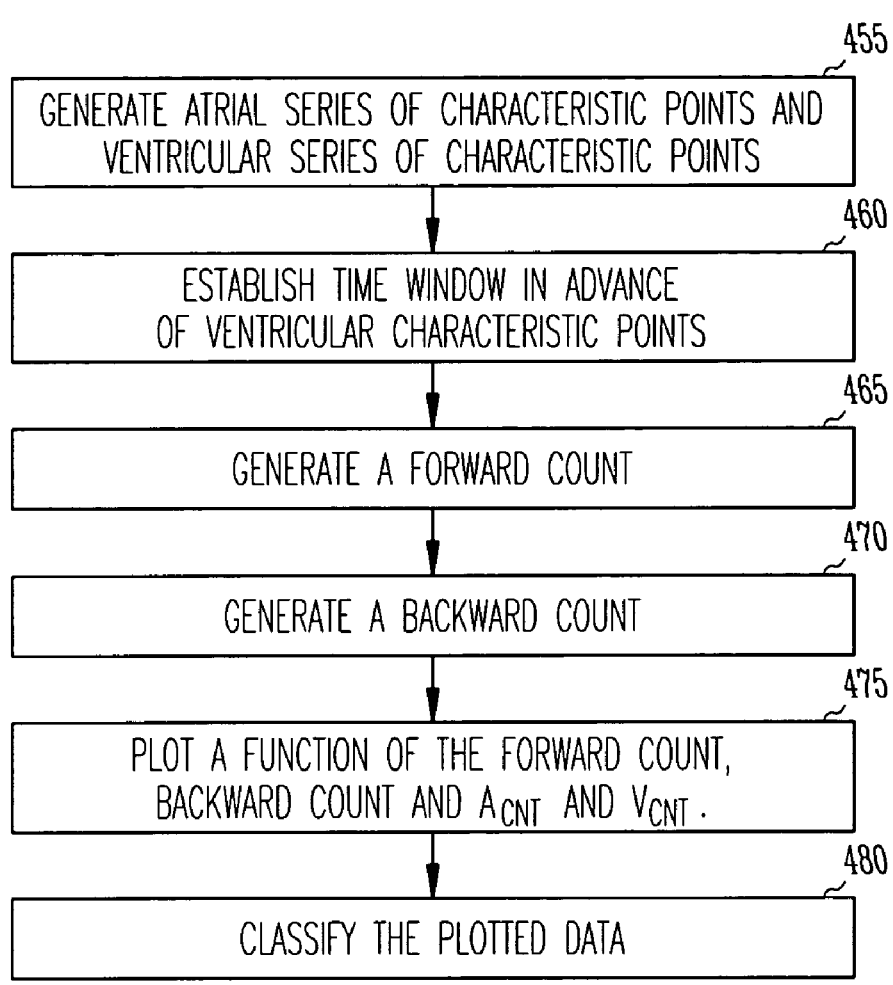
FIG. 13 illustrates a method of discriminating among rhythms according to one embodiment of the present subject matter.

FIG. 13 illustrates exemplary method 450 according to one embodiment of the present subject matter. At 455, an atrial series of characteristic points are generated from an atrial channel and a ventricular series of characteristic points are generated from a ventricular channel. The total number of atrial characteristic points is denoted as $A_{cnt}$ and the total number of ventricular characteristic points is denoted as $V_{cnt}$. At 460, a time window is established in advance of each characteristic point in the ventricular channel. At 465, a backward count is generated by counting, in a single pass through the ventricular series of characteristic points, all ventricular characteristic points that have at least one atrial characteristic point in the window. At 470, a forward count is generated by counting, in a single pass through the ventricular series of characteristic points, all atrial characteristic points that fall into at least one window associated with a ventricular characteristic point. In one embodiment, these counts may be performed in the same single pass through the ventricular characteristic points. At 475, X and Y values are generated based on the forward count, the backward count, $A_{cnt}$ and $V_{cnt}$. In one embodiment, the X-value indicates the backward count expressed as a percentage of all ventricular characteristic points. In one embodiment, the Y-value indicates the ratio of forward count to backward count. In one embodiment, the Y-value indicates $(A:V)*V_{cnt}/A_{cnt}^2$. At 480, the X-Y point is classified to discern a rhythm type. Classification of the data, in one embodiment, includes selecting a separation line or separation contour in the X-Y plane. Data falling on one side of the separation line or contour denotes a particular rhythm type while data on another side denotes a different rhythm type. In one embodiment, a separation line or contour is selected according to methods known as Support Vector Method (SVM) or support vector classification (SVC) (see V. Vapnik. *The Nature of Statistical Learning Theory*. Springer-Verlag, New York, 1995, and others). Factors to consider in placement of a separation line include determining the placement of the line and a slope. Considerations include the proximity of the data points and the width of a separation region between different portions of the X-Y plane. In one embodiment, the X-Y plane is regionalized in a manner that maximizes the separation of data points.

Other embodiments are also contemplated. For example, in one embodiment, a window is established after each atrial characteristic point and counts are established based on the relative timing of atrial characteristic points and ventricular characteristic points.

Other metrics are also contemplated for discriminating among rhythm types. For example, in one embodiment, discrimination is based on the percentage of atrial characteristic points that are not associated with a ventricular characteristic points or a value derived from ventricular characteristic points.

Exemplary Device

In one embodiment, the present subject matter includes circuitry, hardware and software for implantation in a body. In one embodiment, the present subject matter is adapted for use external to a body.

Figure 14:
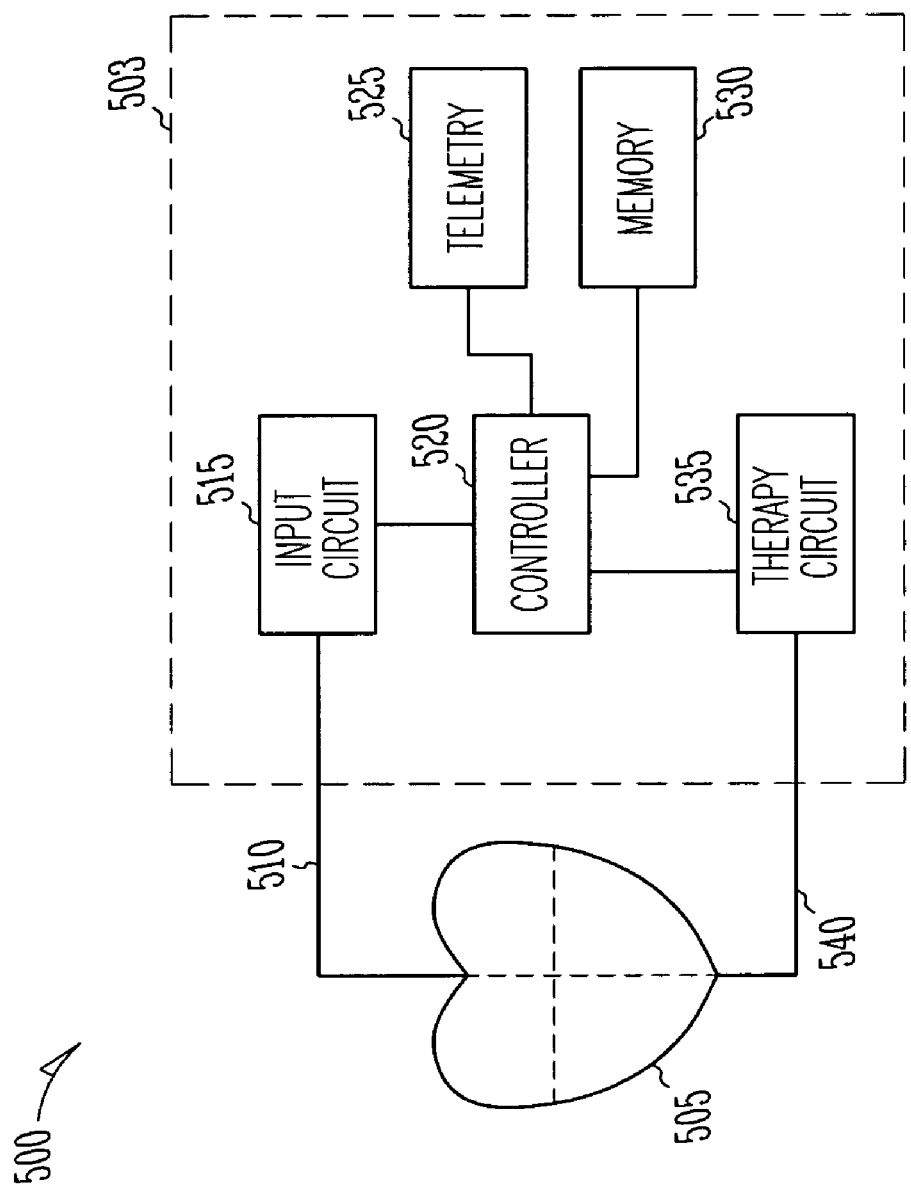
FIG. 14 illustrates a block diagram of an implantable device according to one embodiment of the present subject matter.

FIG. 14 includes a diagram of one embodiment of portions of cardiac rhythm management system 500 according to the present subject matter. As illustrated, system 500 includes unit 503, lead 510 and lead 540, each of which are coupled to heart 505. In various embodiments, unit 503 includes an implantable unit and operates as a pacemaker, a CRT device, a cardioverter/defibrillator, a pacer/defibrillator and a drug delivery device. In the figure, unit 503 senses cardiac activities from heart 505 and delivers therapy to heart 505 according to programming and circuitry of unit 503. Leads 510 and 540 provide electrical connections between unit 503 and heart 505 and each includes an electrode adapted to be disposed in or about heart 505. Lead 510 is coupled to input circuit 515 and provides an electrical signal sensed from cardiac activity of heart 505. Lead 540 provides therapy to heart 505 as a function of a signal received from therapy circuit 535.

In one embodiment, unit 503 includes input circuit 515, controller 520, telemetry circuit 525, memory 530 and therapy circuit 535. Input circuit 515 is coupled to lead 510 and receives an analog signal based on cardiac activity of heart 505. In one embodiment, input circuit 515 includes an analog-to-digital converter.

In one embodiment, controller 520 includes a processor and programming to implement a method as described herein. In one embodiment, controller 520 includes a circuit to control therapy circuit 535 and telemetry circuit 525.

Memory 530 is coupled to controller 520 and provides data storage. In one embodiment, the input signal is sampled and characteristic points are generated substantially in real-time. In one embodiment, characteristic points are generated based on stored sample data derived from the input signal. In one embodiment, programming executing on a processor of controller 520 is stored in memory 530.

In one embodiment, controller 520 determines what therapy or electrical stimulation is to be delivered by therapy circuit 535 to heart 505 using lead 540.

In one embodiment, controller 520 determines what data is to be communicated using telemetry circuit 525. Telemetry circuit 525, in various embodiments is adapted to provide wired or wireless telemetry.

In one embodiment, controller 520 executes programming to determine curvature of an input signal and generates characteristic points.

In one embodiment, controller 520 includes a comparator which generates an output based on a comparison of an input signal and a reference signal. Exemplary comparisons include determining if the lobe is making a positive or negative excursion from a baseline. In one embodiment, an exemplary comparison includes determining if the curvature series lobe is greater or less than a dead-zone threshold. In one embodiment, an exemplary comparison includes comparing the curvature signal with a hysteresis value of a threshold.

In the figure, two leads are shown coupled to heart 505. In one embodiment, a single lead provides both sensing and therapy for heart 505.

System 500, in one embodiment, is adapted to determine a heart rate according to the methods described herein. The heart rate is then stored in memory 530. In one embodiment, the heart rate is used to determine appropriate therapy or to confirm application of a particular therapy. In one embodiment, a first heart rate is determined by a method described herein and a second heart rate is determined by an auxiliary method and controller 520 reconciles the first heart rate and second heart rate to determine a third heart rate. In one embodiment, the heart rate is communicated to a remote programmer by telemetry circuit 525.

System 500, in one embodiment, is adapted to classify a rhythm according to the methods described herein. The rhythm classification is then stored in memory 530. In one embodiment, the classification is used to determine appropriate therapy or to confirm application of a particular therapy. In one embodiment, a first classification is determined by a method described herein and a second classification for the same epoch is determined by an auxiliary method and controller 520 reconciles the first classification and second classification to determine a third classification. In one embodiment, the classification is communicated to a remote programmer by telemetry circuit 525.

ALTERNATIVE EMBODIMENTS

Characteristic points can be described in terms of a size corresponding to the area of a lobe in the curvature series. In one embodiment, before calculating a heart rate or classifying a rhythm type according to a method described herein, the series of characteristic points are filtered based on their size. In one embodiment, this entails selecting only those characteristic points having a size greater than a predetermined value for use in determining a heart rate or rhythm classification. In one embodiment, other filtering criteria is applied to the series of characteristic points before determining a rate or rhythm.

In one embodiment, a rhythm is classified based on a straight line in the X-Y plane. In one embodiment, an irregular shaped region is described in the x-y plane and the cluster of data points in the plane relative to the region provides the basis for discrimination. In one embodiment, probability functions are calculated for the data points and serve as discrimination criteria.

In one embodiment, other discrimination techniques are used in conjunction with those described herein and a processor resolves any differences and makes a classification selection.

In one embodiment, a method described herein is executed by hardwired circuitry. The circuitry may be analog or digital and include circuit elements such as operational amplifiers or logic gates.

CONCLUSION

The above description is intended to be illustrative, and not restrictive. Many other embodiments will be apparent to those of skill in the art upon reviewing the above description.

What is claimed is:

1. An implantable cardiac rhythm management device comprising:
   an input circuit adapted to receive a sampled signal including sampled data points corresponding to cardiac electrical activity;
   a controller coupled to the input circuit and adapted to compute a curvature series using the sample data points, identify lobes each being an excursion of more than a curvature threshold value from a baseline in the computed curvature series, generate a series of characteristic points each associated with a time of a lobe of the identified lobes in the curvature series, and determine a fundamental frequency of the sampled signal by autocorrelating a function of the series of characteristic points, wherein the curvature series includes curvatures each being a non-linear function of first and second derivatives of the sampled signal at one of the sample data points, and the controller is adapted to compute the first and second derivatives and the curvatures; and
   a memory coupled to the controller and adapted to store the fundamental frequency.

2. The device of claim 1 wherein the controller is adapted to determine a size of each characteristic point of the series of characteristic points and determine the fundamental frequency as a function of the determined sizes.

3. The device of claim 1 further comprising a rate estimator coupled to the controller and adapted to generate a beat frequency, and wherein the controller is adapted to generate a heart rate based on the beat frequency and the fundamental frequency.

4. The device of claim 1 further including a telemetry circuit coupled to the controller and adapted to communicate to a programmer.

5. The device of claim 1 further including a therapy circuit coupled to the controller and adapted to deliver electrical stimulation as a function of a signal received from the controller.

6. A method comprising:
   receiving sampled data points representative of a cardiac signal;
   calculating a series of curvatures each as a non-linear function of first and second derivatives of the cardiac signal at one of the sample data points;
   identifying lobes each being an excursion of more than a curvature threshold value from a baseline in the calculated series of curvatures;
   establishing a series of characteristic points each corresponding to a time of occurrence of a lobe of the identified lobes in the series of curvatures;
   using a processor to determine a frequency for the cardiac signal by autocorrelating a function of the series of characteristic points; and
   storing the frequency in a memory.

7. The method of claim 6 wherein the time of occurrence of the lobe includes the time of occurrence of a centroid of the lobe.

8. The method of claim 6 wherein, for each characteristic point of the series of characteristic points, determining a size as a function of an area of the lobe, and wherein using the processor to determine the frequency for the cardiac signal includes determining the frequency as a function of the size of the each characteristic point.

9. The method of claim 6 wherein autocorrelating the function of the series of characteristic points includes autocorrelating a series of time differences for adjacent characteristic points as a function of time of occurrence for each characteristic point.

10. The method of claim 9 wherein autocorrelating the series of time differences for adjacent characteristic points as the function of time of occurrence for each characteristic point includes evaluating a product of a time difference between adjacent characteristic points and a time difference between time shifted adjacent characteristic points.

11. The method of claim 10 wherein the adjacent characteristic points are in time overlap relation with the time shifted adjacent characteristic points.

12. The method of claim 6 wherein autocorrelating the function of the series of characteristic points includes autocorrelating a product of at least two factors selected from the series of characteristic points.

13. A method comprising:
receiving a sampled input signal being a function of sensed cardiac electrical activity;
using a processor to generate a curvature series by computing curvatures each as a non-linear function of first and second derivatives at a sample point of the sampled input signal;
identifying lobes each being an excursion from a baseline in the curvatures series using a curvature threshold value;
generating a series of characteristic points as a function of the curvature series, the characteristic points each associated with a lobe of the identified lobes in the curvature series and having a time as a function of a time of occurrence of the lobe of the identified lobes and a size as a function of an area of the lobe of the identified lobes;
autocorrelating a function of the series of characteristic points to determine a fundamental frequency of the sampled input signal; and
storing the fundamental frequency in a memory coupled to the processor.

14. The method of claim 13 wherein autocorrelating the function includes autocorrelating in a time domain.

15. The method of claim 13 wherein autocorrelating the function includes autocorrelating in a characteristic point domain.

16. The method of claim 13 wherein receiving a sampled signal includes receiving a ventricular rate electrogram, and wherein autocorrelating the function based on the series of characteristic points includes time domain autocorrelating a characteristic point time difference.

17. The method of claim 13 wherein receiving the sampled input signal includes receiving a defibrillation channel electrogram, and wherein autocorrelating the function based on the series of characteristic points includes time domain autocorrelating a characteristic point time difference function.

18. The method of claim 13 further including delivering therapy as a function of the fundamental frequency.

19. An article comprising a machine-accessible medium having associated data wherein the data, when accessed, results in a machine performing:
receiving a sampled cardiac signal including sampled data points representative of the cardiac signal;
generating a curvature series using the sampled data points by computing curvatures each as a non-linear function of first and second derivatives of the sampled cardiac signal at one of the sampled data points;
identifying lobes each being an excursion of more than a curvature threshold value from a baseline in the curvature series;
generating a series of characteristic points in the sampled cardiac signal, each characteristic point corresponding to a lobe of the identified lobes in the curvature series and having a time corresponding to a time of occurrence of the lobe of the identified lobes;
determining a frequency by autocorrelating a function of the series of characteristic points, the frequency including a fundamental frequency of the sampled cardiac signal; and
storing the frequency in a memory.

20. The article of claim 19 wherein the data, when accessed, further results in the machine generating, for each characteristic point of the series of characteristic points, a size determined as a function of the area of the lobe in the curvature series.

21. The article of claim 20 wherein autocorrelating the function of the series of characteristic points includes autocorrelating the function of the series of characteristic points having the size greater than a predetermined value.

22. An article comprising a machine-accessible medium having associated data wherein the data, when accessed, results in a machine performing:
receiving a first sampled signal including first sampled data points and a second sampled signal including second sampled data points, the first and second sampled signals each representing cardiac electrical activity for an epoch;
generating a first curvature series using the first sampled data points by calculating curvatures each as a non-linear function of first and second derivatives of the first sampled signal at one of the first sampled data points;
generating a second curvature series using the second sampled data points by calculating curvatures each being a non-linear function of first and second derivatives of the second sampled signal at one of the second sampled data points;
identifying first lobes each being an excursion from a baseline in the first curvature series using a first curvature threshold value;
identifying second lobes each being an excursion from a baseline in the second curvature series using a second curvature threshold value;
generating a first series of characteristic points in the first sampled signal and a second series of characteristic points in the second sampled signal, each characteristic point in the first series of characteristic points corresponding to a lobe of the identified first lobes and having a time corresponding to a time of occurrence of the lobe of the identified first lobes, each characteristic point in the second series of characteristic points corresponding to a lobe of the identified second lobes and having a time corresponding to a time of occurrence of the lobe of the identified second lobes;
generating a classification of the epoch based on a plot of timewise occurrence of first series characteristic points relative to timewise occurrence of second series characteristic points and a separation contour; and
storing the classification in a memory.

23. The article of claim 22 wherein the data, when accessed, further results in the machine generating, for each characteristic point of the first series of characteristic points and the second series of characteristic points, a size determined as a function of the area of the lobe corresponding to the each characteristic point.

24. The article of claim 22 wherein the data, when accessed, further results in the machine generating a plurality of windows, each window disposed ahead of a characteristic point of the first series of characteristic points.

25. The article of claim 24 wherein generating the classification includes plotting a backward count based on a number of first series characteristic points having at least one second series characteristic point within a window of the plurality of windows and further includes means for determining a forward count based on a number of second series characteristic points disposed within a window of at least one first series characteristic point.

* * * * *